US012747263B2

(12) United States Patent
Nair et al.

(10) Patent No.: US 12,747,263 B2
(45) Date of Patent: Sep. 29, 2026

(54) ORALLY ACTIVE LEUKEMIA INHIBITORY FACTOR (LIF) ANTAGONISTS FOR THE TREATMENT OF CANCER

(71) Applicant: Evestra, Inc., Schertz, TX (US)

(72) Inventors: Hareesh B. Nair, San Antonio, TX (US); Gulzar Ahmed, San Antonio, TX (US); Bindu Santhamma, San Antonio, TX (US); Swapna Konda, San Antonio, TX (US)

(73) Assignee: Evestra, Inc., Schertz, TX (US)

( * ) Notice: Subject to any disclaimer, the term of this patent is extended or adjusted under 35 U.S.C. 154(b) by 376 days.

(21) Appl. No.: 18/263,695

(22) PCT Filed: Jan. 28, 2022

(86) PCT No.: PCT/US2022/070408

§ 371 (c)(1),
(2) Date: Jul. 31, 2023

(87) PCT Pub. No.: WO2022/165512

PCT Pub. Date: Aug. 4, 2022

(65) Prior Publication Data

US 2024/0124515 A1 Apr. 18, 2024

Related U.S. Application Data

(60) Provisional application No. 63/143,565, filed on Jan. 29, 2021.

(51) Int. Cl.

| | |
|---|---|
| ***C07J 9/00*** | (2006.01) |
| ***A61K 31/337*** | (2006.01) |
| ***A61K 31/567*** | (2006.01) |
| ***A61P 35/00*** | (2006.01) |
| ***C07J 1/00*** | (2006.01) |
| ***C07J 41/00*** | (2006.01) |
| ***C07J 43/00*** | (2006.01) |

(52) U.S. Cl.

CPC .......... *C07J 43/003* (2013.01); *A61K 31/337* (2013.01); *A61P 35/00* (2018.01); *C07J 1/0096* (2013.01); *C07J 41/0083* (2013.01); *C07J 41/0094* (2013.01)

(58) Field of Classification Search

CPC ......... C07J 1/0096; C07J 9/00; A61K 31/567; A61P 35/00

USPC .......................................... 552/502; 514/169

See application file for complete search history.

(56) References Cited

U.S. PATENT DOCUMENTS

| | | | |
|---|---|---|---|
| 10,053,485 B2 * | 8/2018 | Nair | A61P 35/00 |
| 10,738,075 B2 * | 8/2020 | Nair | C07J 31/006 |
| 2016/0279145 A1 * | 9/2016 | Nair | C07J 11/00 |
| 2020/0087340 A1 | 3/2020 | Nair et al. | |

FOREIGN PATENT DOCUMENTS

WO WO 2017/112904 A1 6/2017

OTHER PUBLICATIONS

O'Shaughnessy, Jet al.) Superior Survival With Capecitabine Plus Docetaxel Combination Therapy in Anthracycline-Pretreated Patients With Advanced Breast Cancer: Phase III Trial Results. Journal of Clinical Oncology, vol. 20, No. 12, Jun. 15, 2002, doi: 10.1200/JCO.2002.09.002, pp. 2812-2823; abstract; p. 2812, first column first paragraph.

Yue, X et al.) EC330, a small-molecule compound, is a potential novel inhibitor of LIF signaling. Journal of Molecular Cell Biology, vol. 12, No. 6, Jul. 3, 2020, doi: 10.1093/jmcb/mjaa008, pp. 477-480; entire publication.

* cited by examiner

*Primary Examiner* — Charanjit Aulakh

(74) *Attorney, Agent, or Firm* — WOMBLE BOND DICKINSON (US) LLP; Mark R. Deluca

(57) ABSTRACT

Described herein are novel LIF/LIFR inhibitors that exhibit improved cytotoxicity and bioavailability. These LIF/LIFR inhibitors are particularly useful for the treatment of tumors associated with overexpression of LIF.

7 Claims, 9 Drawing Sheets

ORALLY ACTIVE LEUKEMIA INHIBITORY FACTOR (LIF) ANTAGONISTS FOR THE TREATMENT OF CANCER

RELATED APPLICATIONS

This application claims priority to U.S. Provisional Patent Application 63/143,565, filed on Jan. 29, 2021 the contents of which are hereby incorporated by reference in their entirety.

BACKGROUND OF THE INVENTION

Field of the Invention

The invention generally relates to orally active leukemia inhibitory factor (LIF) antagonists for the treatment of malignant and non-malignant cancer.

Description of the Relevant Art

Cancer is characterized by an uncontrolled growth and spread of abnormal cells. According to American Cancer Society, there were 1.8 million new cancer cases diagnosed, and 606,520 cancer deaths, in the United States in 2020. Precision medicine brings great promise to significantly improve the treatment of cancer. A comprehensive array of targeted therapeutics needs to be established to achieve this goal. Currently, there is a substantial need to design drugs targeting not only the drivers for cancer development but also the signaling pathways that are crucial for the maintenance and progression of cancer, as well as the resistance of cancers to treatment. Leukemia inhibitory factor (LIF) is an important cytokine that may be overexpressed in human tumors including solid tumors such as breast cancer, bladder cancer, colorectal cancer, lung cancer, melanoma and nasopharyngeal carcinoma. Recent reports show that targeting LIF signaling can be used to decrease tumorigenesis in many solid tumors.

Leukemia inhibitory factor, or LIF, is an interleukin 6 class cytokine that affects cell growth by inhibiting differentiation. LIF binds to the LIF receptor (LIFR-$\alpha$) which forms a heterodimer with a specific subunit common to all members of that family of receptors, the GP130 signal transducing subunit. This leads to activation of the JAK/STAT (Janus kinase/signal transducer and activator of transcription) and MAPK (mitogen activated protein kinase) cascades. LIF promotes STAT3 phosphorylation (Yu et al., LIF negatively regulates tumor-suppressor p53 through Stat3/ID1/MDM2 in colorectal cancers. Nat Commun. 2014 Oct. 17; 5:5218).

LIF promotes tumorigenesis in many solid tumors and mediates pro-invasive activation of stromal fibroblasts in cancer. LIF mediates TGF beta dependent actinomycin contractility, extracellular matrix remodeling leading to cancer cell invasion in fibroblasts. It is established that paracrine molecules such as TGF-beta, growth factors and proinflammatory molecules such as IL-6 family of cytokines that includes LIF are secreted by cancer cells and promote tumorigenesis. TGF-beta-mediated phosphorylation of Smad3 potentiates transcriptional regulation of many genes that assist in proliferation of cancer cells. The role of TGF-beta/SMAD and JAK/STAT3 signaling in tumor cell dependent proinvasive fibroblast activation and expression of alpha-smooth muscle actin ($\alpha$-SMA), which produces carcinoma associated fibroblast (CAF), has also been established. (Albrengues et al., Epigenetic switch drives the conversion of fibroblasts into proinvasive cancer-associated fibroblasts. Nat Commun. 2015 Dec. 15; 6:10204; Casanova et al. Pramel7 mediates LIF/STAT3-dependent self-renewal in embryonic stem cells. Stem Cells. 2011 March; 29(3): 474-85).

LIF is critically important in sustaining pluripotency, stemcellness and embryogenesis. A critical point during mammalian pregnancy is the implantation of the blastocyst when the embryo attaches to the wall of the uterus. Females lacking a functional LIF gene are fertile, but their blastocysts fail to implant and do not develop. LIF may also be critical to endometrial receptivity in humans, as well as a wide range of other mammals. Reduced LIF expression has been linked to several cases of female infertility (Stewart et al. Blastocyst implantation depends on maternal expression of leukemia inhibitory factor. Nature. 1992 Sep. 3; 359(6390):76-9).

LIF induces many genes that over express in cancer, one of them is breast cancer antiestrogen resistance protein (p13Cas/BCAR1). Overexpression of p130Cas/BCAR1 has been detected in human breast cancer, prostate cancer, ovarian cancer, lung cancer, colorectal cancer, hepatocellular carcinoma, glioma, melanoma, anaplastic large cell lymphoma and chronic myelogenous leukemia. The presence of aberrant levels of hyperphosphorylated p130Cas/BCAR1 strongly promotes cell proliferation, migration, invasion, survival, angiogenesis and drug resistance (Tornillo et al., Cas proteins: dodgy scaffolding in breast cancer. Breast Cancer Res 16, 443 (2014)).

Carcinoma-associated fibroblasts (CAF) are the most abundant population of non-cancer cells found in tumors, and their presence is often associated with poor clinical prognosis. LIF has been found to drive cancer cell-dependent pro-invasive extracellular matrix remodeling in carcinoma associated fibroblasts. It is believed that under the influence of bioactive molecules such as LIF within the tumor stroma, resident fibroblasts are activated, promoting tumorigenesis (Albrengues et al., Epigenetic switch drives the conversion of fibroblasts into proinvasive cancer-associated fibroblasts. Nat Commun. 2015 Dec. 15).

LIF is also an important negative regulator of tumor suppressor gene p53. Down regulation of p53 by LIF is mediated by the activation of STAT3, which transcriptionally induces inhibitor of DNA binding 1 (ID1). ID1 upregulates MDM2, a natural negative regulator of p53 and promotes p53 degradation. EC330 was found to indirectly diminish the phosphorylation of SMAD thorough blocking TGF-beta. Overexpression of LIF is associated with poor prognosis and increase incidence of chemoresistance (Yu et al., LIF negatively regulates tumor-suppressor p53 through Stat3/ID1/MDM2 in colorectal cancers. Nat Commun. 2014 Oct. 17; 5:5218). Targeting LIF and MDM2 to reactivate p53 is a potential therapeutic strategy for chemotherapy as well as in combination with other agents to alleviate chemoresistance.

LIF KO mice have revealed that many of these actions are not apparent during ordinary development (Nicola, N. A. & Babon, J. J. Leukemia inhibitory factor (LIF). *Cytokine Growth Factor Rev* 26, 533-544), indicating a potential therapeutic window for LIF/LIFR axis inhibitors in addition to less toxicity in normal adult tissues. A recent study showed that that LIF is a key paracrine factor from stromal cells acting on cancer cells; and LIF blockade reduce tumor progression; and augment the efficacy of chemotherapy to prolong survival of PDAC (Shi, Y. et al. Targeting LIF-mediated paracrine interaction for pancreatic cancer therapy and monitoring. *Nature* 569, 131-135). Another study also confirmed that blockade of LIF by neutralizing antibodies represents an attractive approach to improving therapeutic outcome in KRAS driven pancreatic cancer (Wang, M. T. et al. Blockade of leukemia inhibitory factor as a therapeutic approach to KRAS driven pancreatic cancer. *Nat Commun* 10, 3055).

Recently, several small molecules that preferentially target LIF/LIFR axis were identified including EC330, EC357, and EC363, which are described in U.S. Pat. No. 10,053,485. Of these molecules, EC330 efficiently inhibited LIF/LIFR mediated proliferation and tumor growth. Molecular docking studies suggest that EC330 targets LIFR21. Further optimization of EC330 to emulate the LIF binding site in LIFR and to improve PK properties resulted in development of first-in-class LIFR inhibitor (EC359). The unique ability of EC359 to bind to a common ligand binding site that block multiple ligands interaction with LIFR, offers an advantage over biologics or small molecules that can only target either of these ligands alone.

Modelling studies predicted that EC359 will interact at the LIF-LIFR binding interface and block interaction of LIF to LIFR. EC359 showed good efficacy in preclinical xenograft and PDX models and has good PK properties. Utilizing pancreatic cell line-derived organoids, EC359 is also shown to be effective in targeting oncogenic LIF/LIFR signaling in pancreatic tumor stroma.

Even though EC359 is established as the lead LIF/LIFR inhibitor molecule, the oral bioavailability is limited to 16% as evident in rodent pharmacokinetic (PK) studies. Oral dosing of LIF inhibitors will enormously increase the patient compliance and development hurdles. It is therefore desirable to have orally active LIF/LIFR inhibitors for the treatment of cancer and other diseases associated with the LIF/LIFR signaling pathway.

SUMMARY OF THE INVENTION

Described herein are novel LIF/LIFR inhibitors that exhibit improved cytotoxicity and bioavailability. These LIF/LIFR inhibitors are particularly useful for the treatment of tumors associated with overexpression of LIF. The LIF/LIFR inhibitors described herein showed LIF specificity and antiproliferative activity in routine screening. These LIF/LIFR inhibitors were further tested to confirm the cytotoxicity in various cancer cell lines. The activity was confirmed dose dependently in ovarian, breast, prostate and endometrial cancer cell lines. Further studies showed the compound to reduce the tumor burden in human triple negative breast cancer (TNBC) xenograft models in mice. The compounds exhibited specificity towards artificially induced LIF overexpressing cells over regular cancer cells.

In an embodiment, an orally available LIF/LIFR inhibitor is used for the treatment of various types of cancers that overexpress leukemia inhibitory factor (LIF).

In an embodiment, the orally available LIF/LIFR inhibitor for the treatment of cancers that overexpress leukemia inhibitory factor (LIF) have the structure (I):

(I)

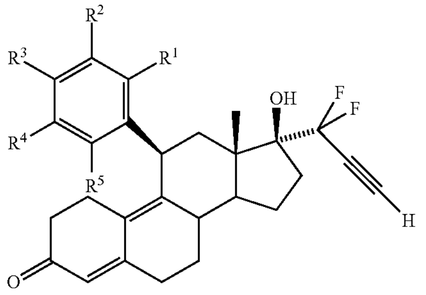

where, $R^1$, $R^2$, $R^3$, $R^4$, and $R^5$ are, independently, H, D, halogen, CN, OH, aryl, alkyl, cycloalkyl, heteroaryl, $-O(CH_2)_n-NR^6R^7$, $-O(CH_2)_n-OR^6$, $-O(CH_2)_n-SR^6$, $-O(CH_2)_n-S(O)R^6$, $-O(CH_2)_n-SO_2R^6$, $-O(CH_2)_n-COOR^6$, $-O(CH_2)_n-CONR^6R^7$, $-O(CH_2)_n-N(R^6)COR^7$, $-OCONR^6R^7$, $-N(R^6)CO_2R^7$, $-OR^6$, $-NR^6R^7$, $-CH(R^6)-OR^7$, $-CONR^6R^7$, $-OD$, or $-CD_3$;

n=1 to 4; and $R^6$ and $R^7$ are, independently, H, alkyl, cycloalkyl, or $CD_3$;

wherein at least one of $R^1$, $R^2$, $R^4$, or $R^5$ is not hydrogen.

In an embodiment, the orally available LIF/LIFR inhibitor for the treatment of cancers that overexpress leukemia inhibitory factor (LIF) have the structure (II):

(II)

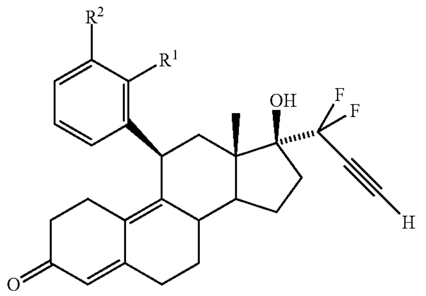

where, $R^1$ and $R^2$ are, independently, H, halogen, CN, OH, aryl, alkyl, cycloalkyl, heteroaryl, $-O(CH_2)_n-NR^6R^7$, $-O(CH_2)_n-OR^6$, $-O(CH_2)_n-SR^6$, $-O(CH_2)_n-S(O)R^6$, $-O(CH_2)_n-SO_2R^6$, $-O(CH_2)_n-COOR^6$, $-O(CH_2)_n-CONR^6R^7$, $-O(CH_2)_n-N(R^6)COR^7$, $-OCONR^6R^7$, $-N(R^6)CO_2R^7$, $-OR^6$, $-NR^6R^7$, $-CH(R^6)-OR^7$, $-CONR^6R^7$, $-OD$, or $-CD_3$;

n=1 to 4;

$R^6$ and $R^7$ are, independently, H, alkyl, cycloalkyl, or $CD_3$;

wherein at least one of $R^1$ or $R^2$ is not hydrogen.

In an embodiment, the orally available LIF/LIFR inhibitor for the treatment of cancers that overexpress leukemia inhibitory factor (LIF) have the structure (III):

(III)

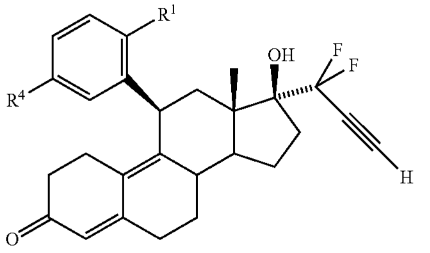

where, $R^1$ and $R^4$ are, independently, H, halogen, CN, OH, aryl, alkyl, cycloalkyl, heteroaryl, $—O(CH_2)_n—NR^6R^7$, $—O(CH_2)_n—OR^6$, $—O(CH_2)_n—SR^6$, $—O(CH_2)_n—S(O)R^6$, $—O(CH_2)_n—SO_2R^6$, $—O(CH_2)_n—COOR^6$, $—O(CH_2)_n—CONR^6R^7$, $—O(CH_2)_n—N(R^6)COR^7$, $—OCONR^6R^7$, $—N(R^6)CO_2R^7$, $—OR^6$, $—NR^6R^7$, $—CH(R^6)—OR^7$, $—CONR^6R^7$, —OD, or $—CD_3$;

n=1 to 4; and $R^6$ and $R^7$ are, independently, H, alkyl, cycloalkyl, or $CD_3$;

wherein at least one of $R^1$ or $R^4$ is not hydrogen.

In an embodiment, the orally available LIF/LIFR inhibitor for the treatment of cancers that overexpress leukemia inhibitory factor (LIF) have the structure (IV):

(IV)

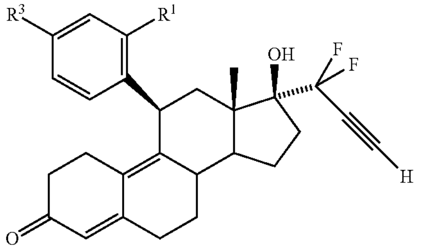

where, $R^1$ is halogen, CN, OH, aryl, alkyl, cycloalkyl, heteroaryl, $—O(CH_2)_n—NR^6R^7$, $—O(CH_2)_n—OR^6$, $—O(CH_2)_n—SR^6$, $—O(CH_2)_n—S(O)R^6$, $—O(CH_2)_n—SO_2R^6$, $—O(CH_2)_n—CONR^6R^7$, $—O(CH_2)_n—COOR^6$, $—O(CH_2)_n—N(R^6)COR^7$, $—OCONR^6R^7$, $—N(R^6)CO_2R^7$, $—OR^6$, $—NR^6R^7$, $—CH(R^6)—OR^7$, $—CONR^6R^7$, —OD, or $—CD_3$;

$R^3$ is H, halogen, CN, OH, aryl, alkyl, cycloalkyl, heteroaryl, $—O(CH_2)_n—NR^6R^7$, $—O(CH_2)_n—OR^6$, $—O(CH_2)_n—SR^6$, $—O(CH_2)_n—S(O)R^6$, $—O(CH_2)_n—SO_2R^6$, $—O(CH_2)_n—COOR^6$, $—O(CH_2)_n—CONR^6R^7$, $—O(CH_2)_n—N(R^6)COR^7$, $—OCONR^6R^7$, $—N(R^6)CO_2R^7$, $—OR^6$, $—NR^6R^7$, $—CH(R^6)—OR^7$, $—CONR^6R^7$, —OD, or $—CD_3$;

n=1 to 4; and $R^6$ and $R^7$ are, independently, H, alkyl, cycloalkyl, or $CD_3$.

In a specific embodiment, the LIF/LIFR inhibitor has the structure (I) where each $R^1$, $R^2$, $R^3$, and $R^4$ are independently H, halogen, lower alkyl, or CN, and wherein at least one of $R^1$, $R^2$, $R^3$, or $R^4$ is not hydrogen. A specific example of a compound of this sub-genus is the compound (D), also referred to herein as EC914.

(D)

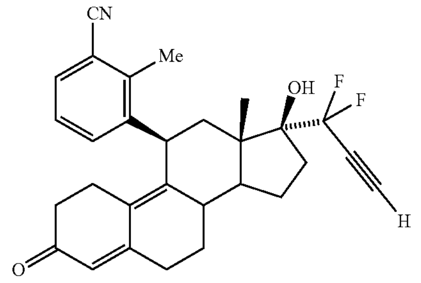

The LIF/LIFR inhibitors described herein exhibit improved oral bioavailability. In an embodiment, the LIF/LIFR inhibitors have an oral bioavailability greater than 20%.

In an embodiment, a pharmaceutical composition comprises a therapeutically effective amount of an LIF/LIFR inhibitor and a pharmaceutically acceptable carrier.

In an embodiment, a method of treating cancers that overexpress leukemia inhibitory factor (LIF) in a subject comprises administering to a subject an effective amount of an LIF/LIFR inhibitor. Exemplary cancers that overexpress LIF include breast cancer, ovarian cancer, prostate cancer, and endometrial cancer.

LIF/LIFR inhibitors exhibit synergistic effects when combined with a taxane chemotherapeutic agent. In an embodiment, a method of treating cancers that overexpress leukemia inhibitory factor (LIF) in a subject comprises administering to a subject an effective amount of an LIF/LIFR inhibitor and a taxane chemotherapeutic agent. In an embodiment, the LIF/LIFR inhibitor has the structure as set forth herein. In an embodiment, the cancer is prostate cancer that overexpresses LIF and the taxane chemotherapeutic agent is docetaxal.

In an embodiment, a chemical intermediate used for the synthesis of alkynyl LIF/LIFR inhibitors have the general structure as shown

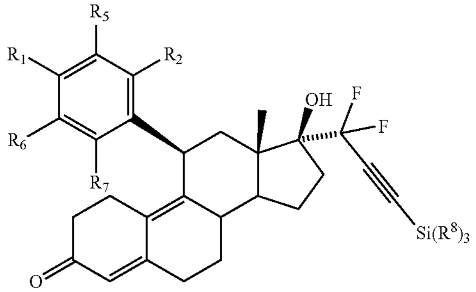

$R^1$, $R^2$, $R^3$, $R^4$, and $R^5$ are, independently, H, D, halogen, CN, OH, aryl, alkyl, cycloalkyl, heteroaryl, $—O(CH_2)_n—NR^6R^7$, $—O(CH_2)_n—OR^6$, $—O(CH_2)_n—SR^6$, $—O(CH_2)_n—S(O)R^6$, $—O(CH_2)_n—SO_2R^6$, $—O(CH_2)_n—COOR^6$, $—O(CH_2)_n—CONR^6R^7$, $—O(CH_2)_n—N(R^6)COR^7$, $—OCONR^6R^7$, $—N(R^6)CO_2R^7$, $—OR^6$, $—NR^6R^7$, $—CH(R^6)—OR^7$, $—CONR^6R^7$, —OD, or $—CD_3$;

n=1 to 4; and $R^6$ and $R^7$ are, independently, H, alkyl, cycloalkyl, or $CD_3$;

wherein at least one of $R^1$, $R^2$, $R^4$, or $R^5$ is not hydrogen.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
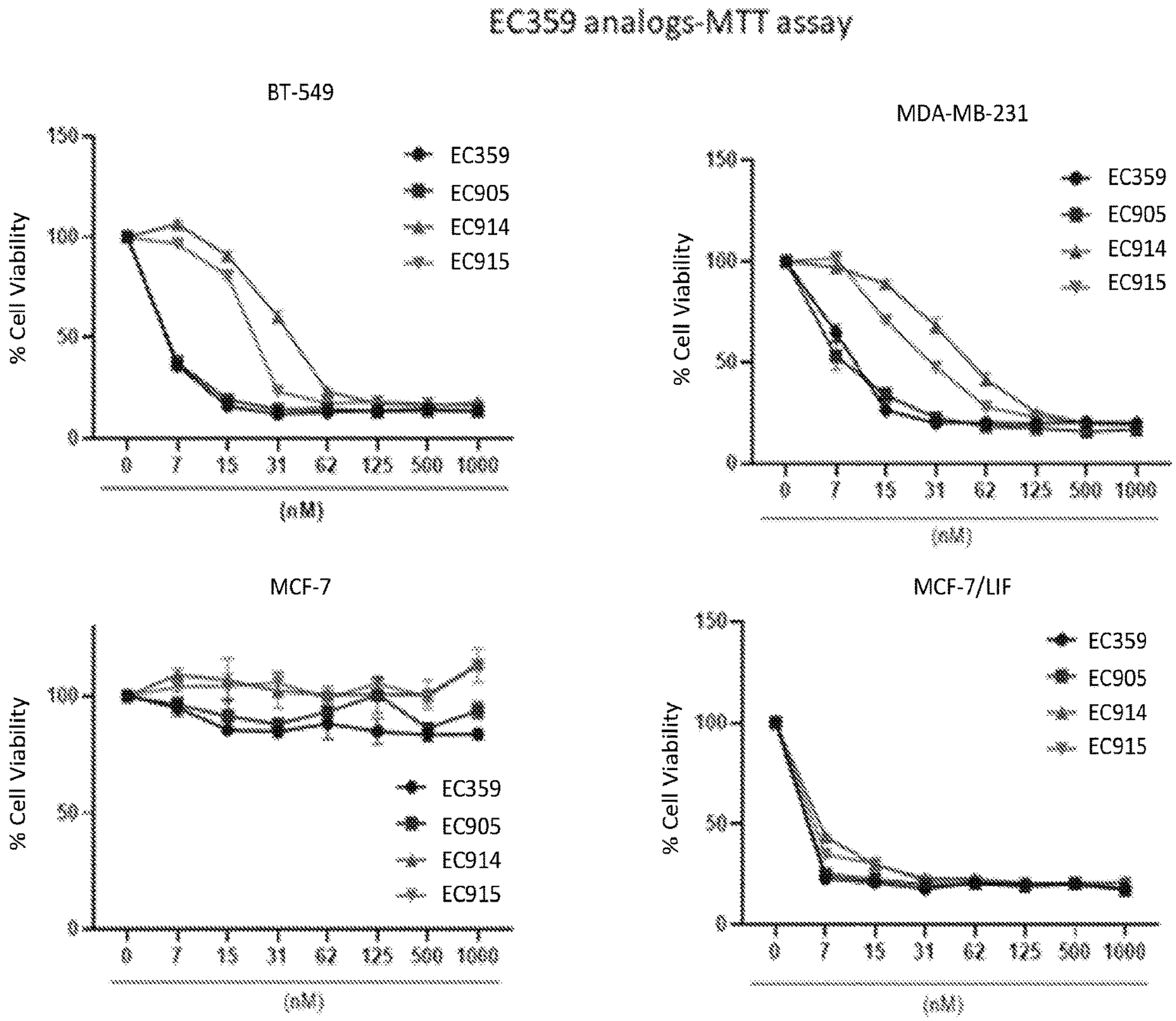
FIG. 1 depicts graphs of the effect of various LIF/LIFR inhibitors against TNBC cells that express LIF and do not express LIF.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular compounds or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Unless defined otherwise, all technical and scientific terms used herein have the same meaning as commonly understood by one of ordinary skill in the art.

Compounds described herein embrace both racemic and optically active compounds. Chemical structures depicted herein that do not designate specific stereochemistry are intended to embrace all possible stereochemistries.

It will be appreciated by those skilled in the art that compounds having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound. As used herein, the term "single stereoisomer" refers to a compound having one or more chiral center that, while it can exist as two or more stereoisomers, is isolated in greater than about 95% excess of one of the possible stereoisomers. As used herein a compound that has one or more chiral centers is considered to be "optically active" when isolated or used as a single stereoisomer.

The term "alkyl" as used herein generally refers to a chemical substituent containing the monovalent group $C_nH_{2n}$, where n is an integer greater than zero. In some embodiments n is 1 to 12. The term "alkyl" includes a branched or unbranched monovalent hydrocarbon radical. Examples of alkyl radicals include, but are not limited to: methyl, ethyl, propyl, isopropyl, butyl, iso-butyl, sec-butyl, pentyl, 3-pentyl, hexyl, heptyl, octyl, nonyl, decyl, undecyl, dodecyl. When the alkyl group has from 1-6 carbon atoms, it is referred to as a "lower alkyl." Suitable lower alkyl radicals include, but are not limited to, methyl, ethyl, n-propyl, i-propyl, 2-propenyl (or allyl), n-butyl, t-butyl, and i-butyl (or 2-methylpropyl).

The term "cycloalkyl" generally refers to refers to a saturated ring having 3 to 7 carbon atoms as a monocycle, 7 to 12 carbon atoms as a bicycle, and up to about 20 carbon atoms as a polycycle. Monocyclic cycloalkyls have 3 to 7 ring atoms, still more typically 5 or 6 ring atoms. Bicyclic carbocycles have 7 to 12 ring atoms, e.g., arranged as a bicyclo 4.5, 5.5, 5.6 or 6.6 system, or 9 or 10 ring atoms arranged as a bicyclo 5.6 or 6.6 system, or spiro-fused rings. Non-limiting examples of monocyclic cycloalkyls include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl.

The term "aryl" is used to refer to an aromatic substituent which may be a single ring or multiple rings which are fused together, linked covalently, or linked to a common group such as an ethylene moiety. Aromatic ring(s) include but are not limited to phenyl, naphthyl, biphenyl, diphenylmethyl, and 2,2-diphenyl-1-ethyl. The aryl group may also be substituted with substituents including, but not limited to, alkyl groups, halogen atoms, nitro groups, carboxyl groups, alkoxy, and phenoxy to give a "substituted aryl group." Substituents may be attached at any position on the aryl radical which would otherwise be occupied by a hydrogen atom.

The term "heterocycle" as used herein generally refers to a non-aromatic closed-ring structure, in which one or more of the atoms in the ring is an element other than carbon. The term "heteroaryl" refers to an aromatic closed-ring structure, in which one or more of the atoms in the ring is an element other than carbon. Heteroaryls include, but are not limited to, rings such as thiophene, pyridine, isoxazole, phthalimide, pyrazole, indole, furan, or benzo-fused analogs of these rings. Examples of heterocycles include, but are not limited to, tetrahydrofuran, morpholine, piperidine, pyrrolidine, and others. Also included are fused ring and spiro compounds containing a heterocycle or a heteroaryl.

The term "pharmaceutically acceptable salts" includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

The present invention relates to orally administered LIF/LIFR inhibitors as anti-cancer compounds, acting through inhibition of leukemia inhibitory factor (LIF) or leukemia inhibitory factor receptor (LIFR). One significant advantage of the described compounds is that they can be developed into orally administered compounds to act directly on the tumor cells/tumor stem cells and on the surrounding stromal fibroblasts (tumors with desmoplastic stroma or hypertrophic cell mass) as well.

In an embodiment, an orally available LIF/LIFR inhibitor for the treatment of various types of tumors that overexpress LIF has the structure (I):

(I)

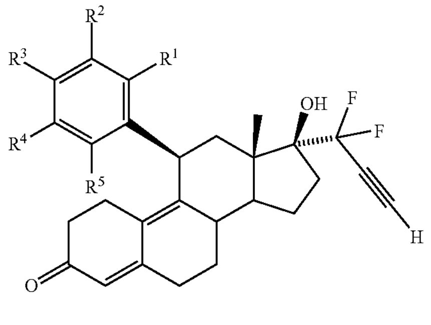

where, $R^1$, $R^2$, $R^3$, $R^4$, and $R^5$ are, independently, H, D, halogen, CN, OH, aryl, alkyl, cycloalkyl, heteroaryl, heterocycle, $—O(CH_2)_n—NR^6R^7$, $—O(CH_2)_n—OR^6$, $—O(CH_2)_n—SR^6$, $—O(CH_2)_n—S(O)R^6$, $—O(CH_2)_n—SO_2R^6$, $—O(CH_2)_n—COOR^6$, $—O(CH_2)_n—CONR^6R^7$, $—O(CH_2)_n—N(R^6)COR^7$, $—OCONR^6R^7$, $—N(R^6)CO_2R^7$, $—OR^6$, $—NR^6R^7$, $—CH(R^6)—OR^7$, $—CONR^6R^7$, —OD, or $—CD_3$;

n=1 to 4; and $R^6$ and $R^7$ are, independently, H, alkyl, cycloalkyl, or $CD_3$;

where at least one of $R^1$, $R^2$, $R^4$, or $R^5$ is not hydrogen.

In an embodiment, an orally available LIF/LIFR inhibitor for the treatment of various types of tumors that overexpress LIF has the structure (II):

(II)

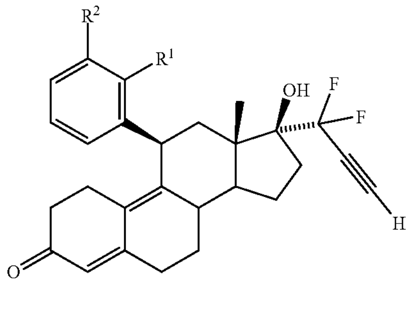

where, $R^1$ and $R^2$ are, independently, H, halogen, CN, OH, aryl, alkyl, cycloalkyl, heteroaryl, heterocycle, $—O(CH_2)_n—NR^6R^7$, $—O(CH_2)_n—OR^6$, $—O(CH_2)_n—SR^6$, $—O(CH_2)_n—S(O)R^6$, $—O(CH_2)_n—SO_2R^6$, $—O(CH_2)_n—COOR^6$, $—O(CH_2)_n—CONR^6R^7$, $—O(CH_2)_n—N(R^6)COR^7$, $—OCONR^6R^7$, $—N(R^6)CO_2R^7$, $—OR^6$, $—NR^6R^7$, $—CH(R^6)—OR^7$, $—CONR^6R^7$, —OD, or $—CD_3$;

n=1 to 4; and $R^6$ and $R^7$ are, independently, H, alkyl, cycloalkyl, or $CD_3$;

where at least one of $R^1$ or $R^2$ is not hydrogen.

In an embodiment, an orally available LIF/LIFR inhibitor for the treatment of various types of tumors that overexpress LIF has the structure (III):

(III)

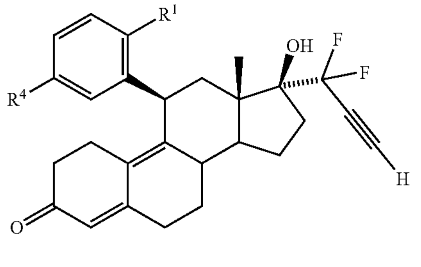

where, $R^1$ and $R^4$ are, independently, H, halogen, CN, OH, aryl, alkyl, cycloalkyl, heteroaryl, heterocycle, $—O(CH_2)_n—NR^6R^7$, $—O(CH_2)_n—OR^6$, $—O(CH_2)_n—SR^6$, $—O(CH_2)_n—S(O)R^6$, $—O(CH_2)_n—SO_2R^6$, $—O(CH_2)_n—COOR^6$, $—O(CH_2)_n—CONR^6R^7$, $—O(CH_2)_n—N(R^6)COR^7$, $—OCONR^6R^7$, $—N(R^6)CO_2R^7$, $—OR^6$, $—NR^6R^7$, $—CH(R^6)—OR^7$, $—CONR^6R^7$, —OD, or $—CD_3$;

n=1 to 4; and $R^6$ and $R^7$ are, independently, H, alkyl, cycloalkyl, or $CD_3$;

wherein at least one of $R^1$ or $R^4$ is not hydrogen.

In another embodiment, an orally available LIF/LIFR inhibitor for the treatment of various types of tumors that overexpress LIF has the structure (IV):

(IV)

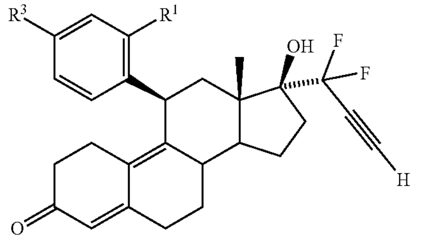

where, $R^1$ is halogen, CN, OH, aryl, alkyl, cycloalkyl, heteroaryl, heterocycle, $—O(CH_2)_n—NR^6R^7$, $—O(CH_2)_n—OR^6$, $—O(CH_2)_n—SR^6$, $—O(CH_2)_n—S(O)R^6$, $—O(CH_2)_n—SO_2R^6$, $—O(CH_2)_n—COOR^6$, $—O(CH_2)_n—CONR^6R^7$, $—O(CH_2)_n—N(R^6)COR^7$, $—OCONR^6R^7$, $—N(R^6)CO_2R^7$, $—OR^6$, $—NR^6R^7$, $—CH(R^6)—OR^7$, $—CONR^6R^7$, —OD, or $—CD_3$;

$R^3$ is H, halogen, CN, OH, aryl, alkyl, cycloalkyl, heteroaryl, $—O(CH_2)_n—NR^6R^7$, $—O(CH_2)_n—OR^6$, $—O(CH_2)_n—SR^6$, $—O(CH_2)_n—S(O)R^6$, $—O(CH_2)_n—SO_2R^6$, $—O(CH_2)_n—COOR^6$, $—O(CH_2)_n—CONR^6R^7$, $—O(CH_2)_n—N(R^6)COR^7$, $—OCONR^6R^7$, $—N(R^6)CO_2R^7$, $—OR^6$, $—NR^6R^7$, $—CH(R^6)—OR^7$, $—CONR^6R^7$, —OD, or $—CD_3$;

n=1 to 4; and $R^6$ and $R^7$ are, independently, H, alkyl, cycloalkyl, or $CD_3$.

In a specific embodiment, the LIF/LIFR inhibitors have the structure (I) where each $R^1$, $R^2$, $R^3$, and $R^4$ are independently H, halogen, lower alkyl, or CN, and at least one of $R^1$, $R^2$, $R^3$, or $R^4$ is not hydrogen. Specific LIF/LIFR inhibitors include compounds (A)-(H).

(A)

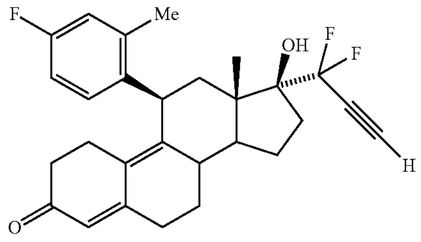

(B)

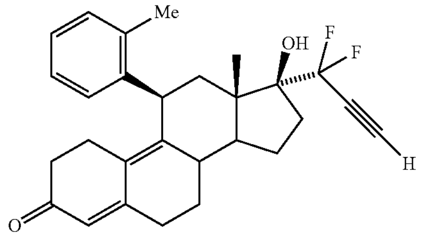

(C)

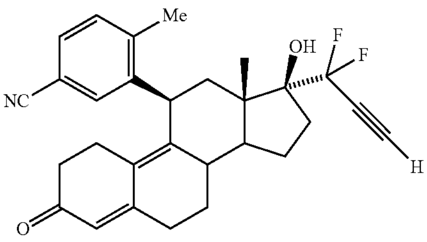

-continued (D)

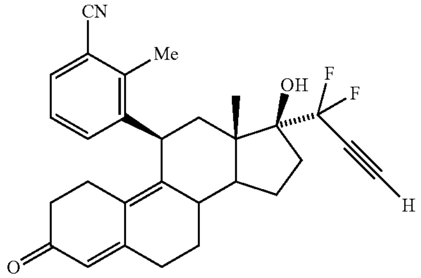

(E)

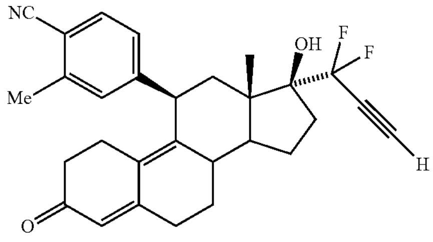

(F)

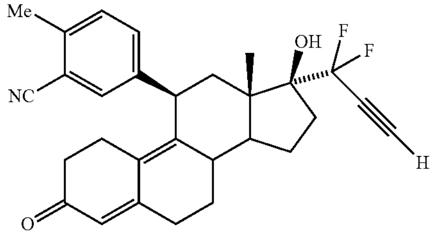

(G)

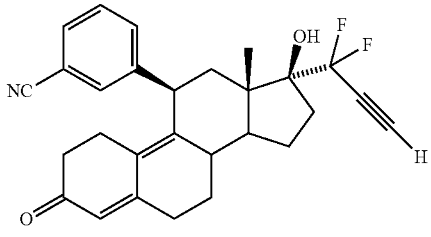

(H)

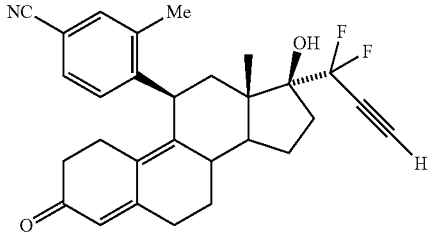

In a specific embodiment, the LIF/LIFR inhibitors have the structure (I) where $R^2$ is $—O(CH_2)_n—COOR^6$, $—O(CH_2)_n—NR^6R^7$, or $—O(CH_2)_n—OR^6$ and each of $R^1$, $R^3$, $R^4$, or $R^5$ is hydrogen. Specific LIF/LIFR inhibitors include compounds (I)-(K).

(I)

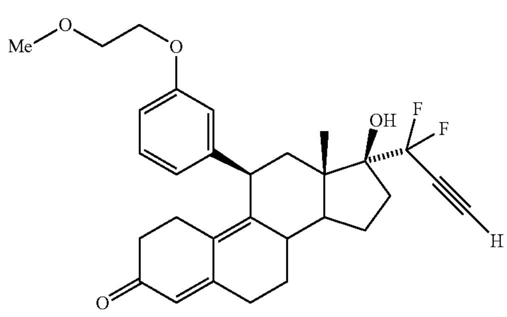

(J)

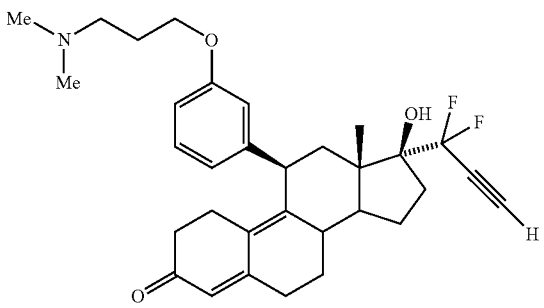

(K)

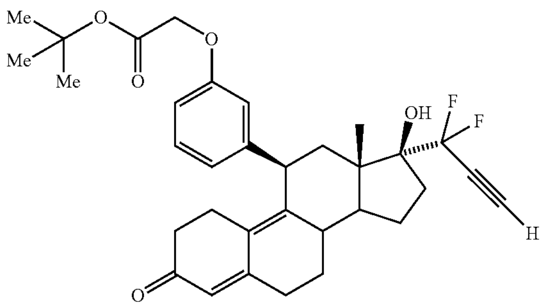

In a specific embodiment, the LIF/LIFR inhibitors have the structure (I) where $R^1$ is a heteroaryl, and each of $R^2$, $R^3$, $R^4$, and $R^5$ is hydrogen. A specific LIF/LIFR inhibitor having this structure is compound (L).

(L)

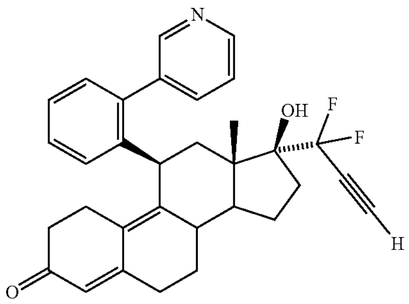

Compounds having the structures (I)-(IV), including specific compounds (A)-(L), exhibit improved oral bioavailability compared to other structurally similar LIF inhibitors. In an embodiment, compounds useful for the treatment of cancer in a subject have an oral bioavailability greater than 20%, or greater than 30%, or greater than 40%, or greater than 50%, or greater than 60%, or greater than 70%, or greater than 80%. Generally, oral bioavailability is determined as a ratio of amount of compound that reaches systemic circulation when administered orally to the amount of compound that reaches systemic circulation when administered intravenously (iv). For example, the oral bioavailability can be determined by the formula (1):

$$F=100*(AUC_{po}*D_{iv}/AUC_{iv}*D_{po}) \quad (1)$$

where: F is bioavailability; $AUC_{po}$ is dose-corrected area under curve of non-intravenous oral drug; $D_{iv}$ is the intravenous dose; $AUC_{iv}$ is the area under the curve intravenous; and $D_{po}$ is the oral dose.

The cytotoxicity and bioavailability of the compounds described herein make the LIF/LIFR inhibitors particularly useful for the treatment of tumors associated with overexpression of LIF. In an embodiment, a compound having any of the structures (I)-(IV) can be used for treating a subject suffering from cancer that overexpresses LIF. The method includes administering to the subject a therapeutically effective amount of an LIF/LIFR inhibitor having any of the structures (I)-(IV) to the subject to treat the cancer. LIF/LIFR inhibitors having the above structures (I)-(IV), including specific compounds (A)-(L), showed LIF specificity and antiproliferative activity in routine screening. These LOIF/LIFR inhibitors were further tested to confirm the cytotoxicity in various cancer cell lines. The activity was confirmed dose dependently in ovarian, breast, prostate and endometrial cancer cell lines. Further studies showed the compound to reduce the tumor burden in human triple negative breast cancer (TNBC) xenograft models in mice. The compounds exhibited specificity towards artificially induced LIF overexpressing cells over regular cancer cells.

In an embodiment, the LIF/LIFR inhibitors described herein are administered as a pharmaceutical composition. A pharmaceutical composition comprises a therapeutically effective amount of an LIF/LIFR inhibitor as described herein and a pharmaceutically acceptable carrier. Preferred pharmaceutical compositions are compositions designed for oral administration. Any suitable route of oral administration may be employed for providing a patient with an effective dosage of the compounds described herein. Oral dosage forms include, but are not limited to tablets, troches, dispersions, suspensions, solutions, or capsules.

The compounds described herein can be formulated or oral use with conventional carriers and excipients, which will be selected in accord with ordinary practice. Tablets will contain excipients, glidants, fillers, binders and the like. Aqueous formulations are prepared in sterile form. All formulations will optionally contain excipients such as those set forth in the "Handbook of Pharmaceutical Excipients" (1986).

Pharmaceutical formulations comprise at least one active ingredient, as above defined, together with one or more acceptable carriers therefor and optionally other therapeutic ingredients. The carrier(s) must be "acceptable' in the sense of being compatible with the other ingredients of the formulation and physiologically innocuous to the recipient thereof. The formulations include those suitable for oral administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). In general, the formulations are prepared by uniformly and intimately bringing into association the active ingredient with liquid carriers or finely divided solid carriers or both, and then, if necessary, shaping the product. Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. For example, tablets may be coated by known techniques including microencapsulation to delay disintegration and adsorption in the gastrointestinal tract and thereby provide a sustained action over a longer period.

The LIF/LIFR inhibitors described herein also show synergistic properties when used with taxane chemotherapeutic agents. In one embodiment, a combination of a LIF/LIFR inhibitor and a taxane chemotherapeutic agent is useful for the treatment of prostate cancer cell lines that overexpress LIF. In a specific embodiment, the taxane chemotherapeutic agent is docetaxal.

In one test, NE-1.8 (neuro endocrine-like) prostate cancer cell line was treated with compound 12 (EC914).

12

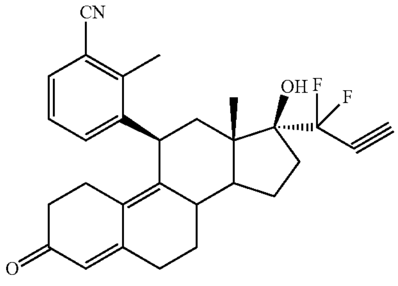

After 96 hours, the cell viability was observed using Calcein AM fluorescent dye-based cell viability assay. More than 50-80% of cell growth inhibition was observed from 50 nM to 250 nm concentration of EC914 compared to vehicle control. Similar growth inhibition trend was observed upon treatment with LIF inhibitor on the C42B prostate cancer cell line at 48 hrs.

Orally active analogues of EC359 such as EC914 show potent antiproliferative activity in triple negative breast cancer cells. Also, these compounds were highly selective in TNBC cells that express LIF, contrary to MCF-7 cells, as shown below. The artificial expression of LIF in MCF7 cells (MCF7/LIF) made those cells vulnerable to LIF inhibitors (FIG. 1) such as compound 5 (EC905) and compound 13 (EC915)

5

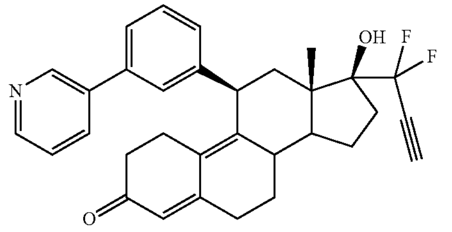

13

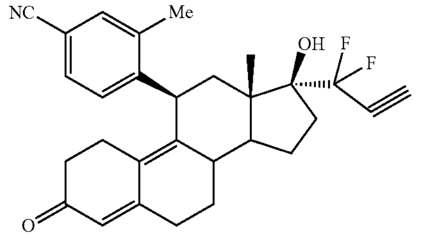

Figure 2:
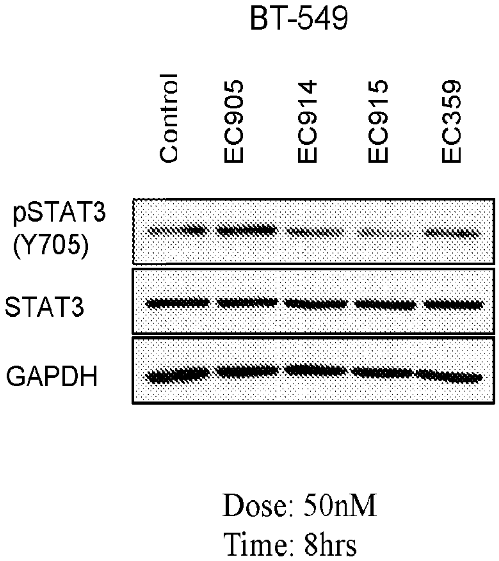
FIG. 2 depicts a Western blot analysis of various LIF/LIFR inhibitors against pSTAT3, STAT3, and GAPDH.
Figure 3:
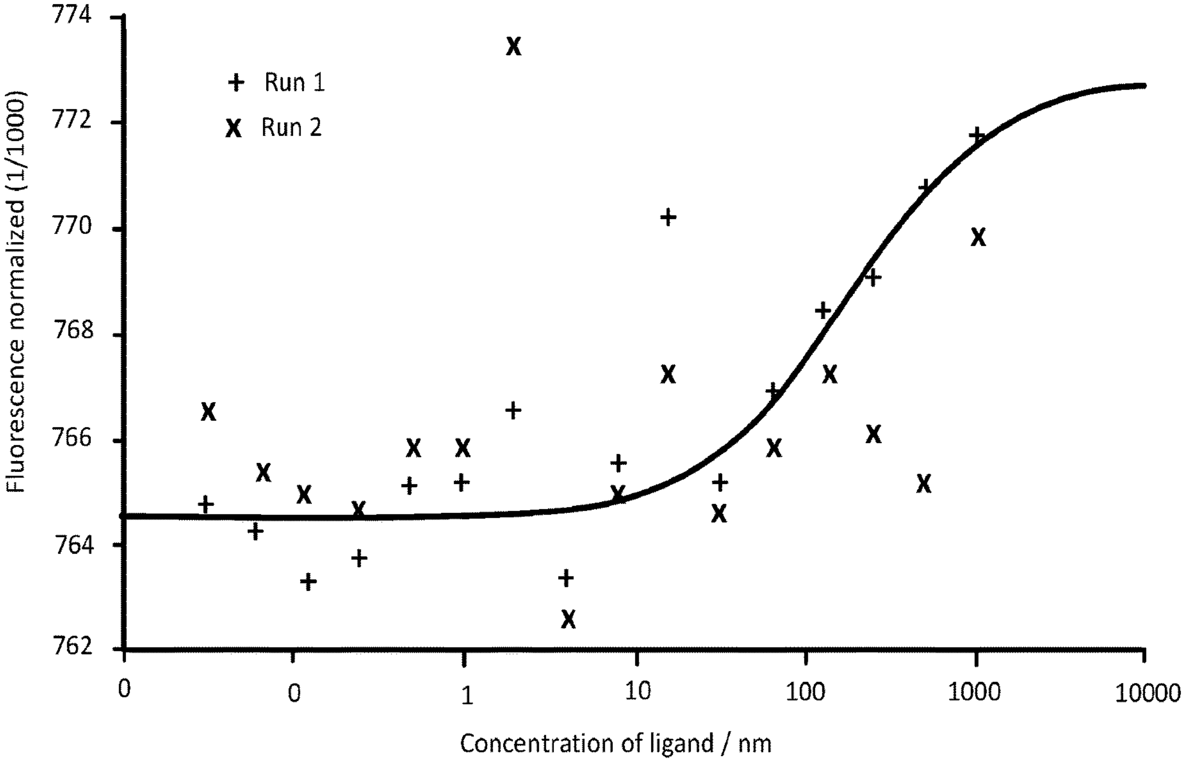
FIG. 3 depicts a binding plot of EC914 to LIFR measured by microscale thermophoresis (MST)

The orally active LIF inhibitors such as EC914 showed reduced STAT3 phosphorylation as immediate downstream of LIF activity (FIG. 2). It is believed that EC914 binds directly to LIFR and blocks LIF signaling. Binding of EC914 to LIFR was measured by microscale thermophoresis (MST). The binding kD was 174 nM (FIG. 3).

Figure 4:
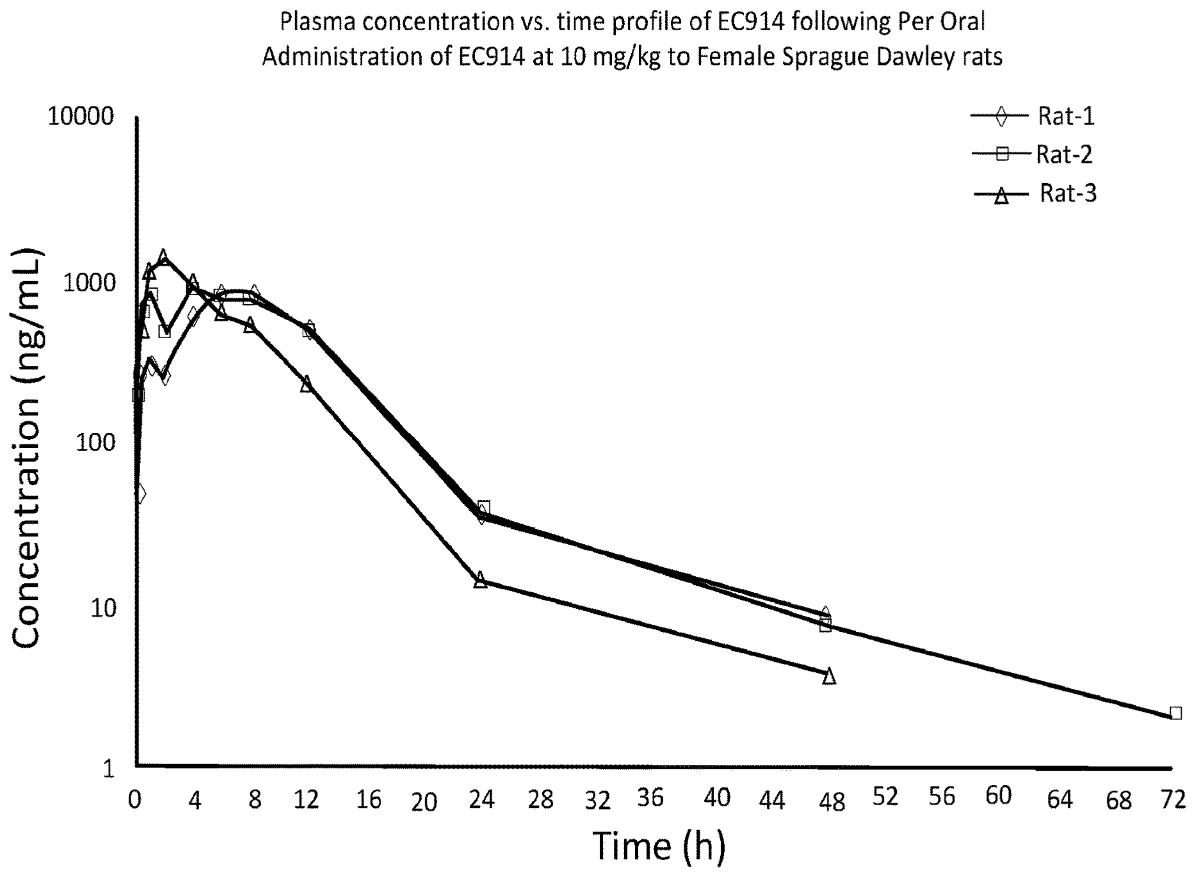
FIG. 4 depicts a plasma concentration vs. time profile of EC 914 during oral administration.
Figure 5:
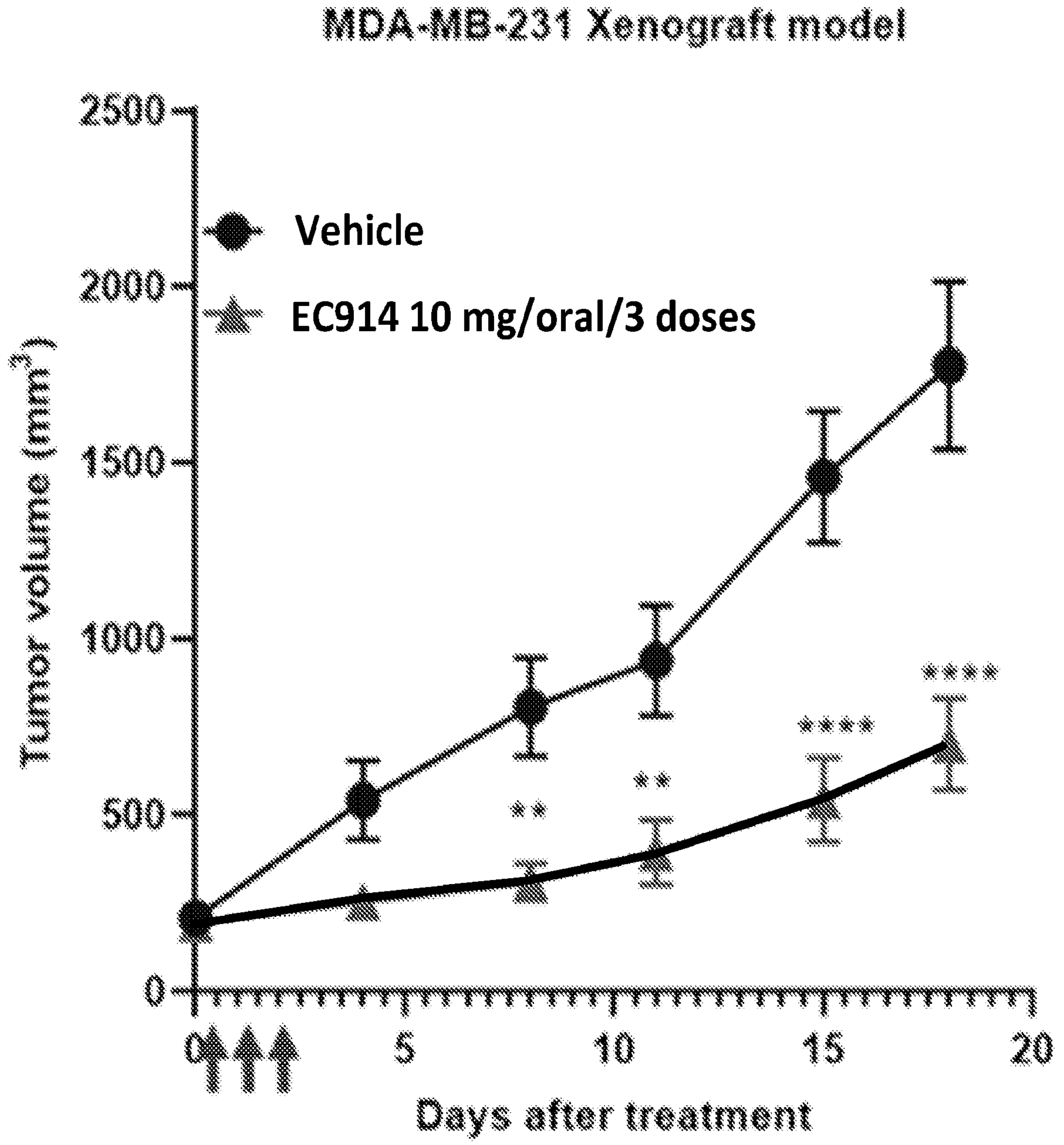
FIG. 5 depicts a plot of reduction in tumor volume by EC914 in a MDA-MB-231 xenograft model.

EC914 has a high oral bioavailability of 87.94% as shown in PK studies in Sprague Dawley rats (FIG. 4). EC914 reduced tumors burden in TNBC mouse xenograft model with Initial 3 doses of 10 mg/kg (FIG. 5). The chemical properties of various LIF inhibitors are compared in Table 1.

TABLE 1

| Compounds | EC914 | EC359 |
|---|---|---|
| Molecular weight | 461.54 | 540.68 |
| Oral bioavailability | 87.9% | 16% |
| cLogP | 4.85 | 8.09 |
| LIFR binding | 175 nM | 10.2 nM |
| Administration Route | Oral | IV |
| Binding to other steroid receptors | No | Low binding to PR |

Biology Tests.

Cytotoxicity Assays

In order to identify the mechanism of action of EC914, we checked cytotoxicity of these compounds in various cells lines and derived IC50 values. Briefly, $5\times10^3$ cells were seeded in 96-well plates and incubated with compounds (0.0001-10 μmol/L) or dimethyl sulfoxide (DMSO; 0.02% v/v) for 24, 48, and 72 hours at 37° C. and cell viability was measured using a Fluoroscan plate reader (Nair et al. Estrogen receptor-β activation in combination with letrozole blocks the growth of breast cancer tumors resistant to letrozole therapy. Steroids. 2011 July; 76(8):792-6).

Soft Agar Colony Formation Assay

Colonies of cancer cells formed soft agar in the presence and absence of the testing compounds is a standard assay to interpret in-vitro tumorigenic potential. in the Basal layer of agar was prepared by mixing 1% DNA grade agar melted and cooled to 40° C. with an equal volume of (2×) Dulbecco's Modified Eagle's Medium (DMEM) to obtain 0.5% agar that was dispersed in a 6-well plate and allowed to solidify. A total of 0.6% agar was prepared in RPMI medium and mixed together with T47D cells ($0.5\times10^6$ cells/mL) and immediately plated on the basal layer in the presence or absence of testing compounds. The cultures were incubated at 37° C. in a $CO_2$ incubator for 2 weeks, and colonies were stained with 0.005% crystal violet and observed under a light microscope.

Apoptosis Assay

Caspase-3/7 activity in HESE cells was measured using Caspase-Glo assay kit (Promega), as described before (Bhaskaran et al, 2013). Briefly, cells were homogenized in homogenization buffer (25 mmol/L HEPES, pH 7.5, 5 mmol/L $MgCl_2$, and 1 mmol/L EGTA), protease inhibitors, and the homogenate was centrifuged at 13,000 rpm at 4° C. for 15 minutes. To 10 μL of the supernatant containing protein was added to an equal volume of the assay reagent and incubated at room temperature for 2 hours. The luminescence was measured using a luminometer. The percent of apoptosis induced by treatment with EC914 is comparable to that of EC359, a less orally available LIF inhibitor developed by us previously EC914 induce apoptosis and reduces STAT3 phosphorylation.

Western Blotting

In brief, MDA-MB-231/BT549 cells were treated with compounds for 3 days at different concentrations (10, 100 nM) and cell lysates were separated by 8% SDS-PAGE and transferred to polyvinylidene difluoride membranes. Membranes were then incubated with primary antibodies including phosphorylated and/or total pSTAT3. After overnight incubation at 4° C., membranes were incubated with secondary antibodies. Immunoreactive bands were then visualized by the enhanced chemiluminescence (ECL) detection system (GE healthcare.

Tumor Xenograft Study

Uniform suspensions of human breast cancer MDA-MB-231 cells ($2\times10^6$) in 100 μL (0.02 carboxymethyl cellulose in phosphate buffered saline) were injected subcutaneously into the right and left flanks of 4- to 5-week-old female athymic nude mice (Charles River Laboratories). After 10 days, when the tumor diameter reaches 100 $mm^3$, the mice were randomly allocated to 3 groups of each containing 6 animals. Group 1 served as the untreated control, groups 2 received EC914 orally at 10 mg/kg daily for 3 doses. All drug was formulated in a vehicle containing 58.5% Labrasol ALF, 22.5% Labrafil M, 1944 CS, 9% Capryol 90 and 10% water q.s. Tumors were allowed to reach palpability before drug intervention. Tumor size was measured every 3 days using digital Vernier Calipers and tumor volume was calculated using the ellipsoid formula [D×(d2)]/2, where D is the large diameter of the tumor and d represents the small diameter. On day 19, the mice were euthanized, and tumors were harvested for protein and gene expression studies since the control tumors reached maximum allowable size as the IACUC regulations (See FIG. 5).

Pharmacokinetic Study

To assess the pharmacokinetic (PK) properties of the compounds, male C57 mice (n=10 per sex) were given 2 mg/kg (i.v) and 5 mg/kg (p.o) of the compound or vehicle. The doses for the PK studies were chosen based on preliminary in vivo preclinical studies of parent compound EC359 and EC914 in rats. Bioavailability (% F) is assessed at various time points after administering EC914 and its metabolites. Blood samples will be collected at 5, 15, 30, and 45 min and 1, 2, 4, 6, 12, 24 h after drug administration. The plasma fraction will be isolated and stored at −20° C. until LC/MS/MS analysis, and all standard PK parameters will be determined, including Cmax=maximum plasma drug concentration obtained after i.v and p.o. administration of a drug between the time of dosing and the final observation point; Tmax=time at maximum observed plasma concentration (Cmax) noted in minutes after administration of the drug; T½=terminal elimination half-life from both IV and non-IV dosing; VZ=volume of distribution calculated based on the terminal phase plasma data from IV dosing; VSS=an estimate of the volume of distribution as steady-state; CL=total body clearance is a measurement of the availability of the body to remove the drug from the plasma.

Syngeneic Mouse Model

A series of murine syngeneic PCa cell lines derived from Pten cKO and Pten cKO, and Hi Myc activated mice models was developed. Luciferase-tagged mPCa cells will be orthotopically implanted in the C57 mouse prostate and treated with a treatment schedule and drug dosage described in C.1.5.3. In addition to IVIS imaging, syngeneic PCa growth will be monitored by the Visual Sonic imaging system using echo measurements before and after therapeutic intervention. After three post-treatment weeks, mice from all the groups will be sacrificed, and tumors will be harvested and digested using collagenase. Harvested tumors will be weighed and cut into three portions, with one to be used for quantification of side population using FACS analysis (digested with collagenase), and the other two portions will be used for western blot analysis (pulverized in liquid nitrogen) and formalin-fixed to analyze LIFR and its downstream and CSC markers using IHC.

Results

Treating castration-resistant prostate cancer (CRPC) is a major clinical hurdle characterized by increased metastasis. At the time of CRPC diagnosis, 15% of patients had undergone distant metastases to bone, and 80% of patients with the organ-confined disease may not respond to local therapy, which may undoubtedly contribute to highly metastatic castration-resistant prostate cancer (mCRPC). Among the currently available chemotherapeutic modalities for CRPC, docetaxel (DTX) still dominates in the first-line settings for patients with localized prostate cancer. However, DTX has many limitations due to its inability to (a) control tumor microenvironment, (b) cancer stem cells (CSC), and (c) signaling to contribute therapy resistance, disease relapse, and tumor aggressiveness. Recent findings demonstrate that leukemia inhibitory factor (LIF) and its receptor (LIFR) signaling were activated after androgen deprivation therapy (ADT). Specifically, LIFR phosphorylation at serine 1044 was reported to be associated with activity, oncogenic function, and metastasis. In addition, overexpression of LIFR was also observed in several cancers, including CRPC. Furthermore, LIFR plays a major role in the enrichment and maintenance of CSCs, which is a critical factor for tumor recurrence and metastasis. Therefore, it is important to suppress the expression of LIFR signaling to prevent therapy resistance and metastasis in CRPC. Our preliminary data shows proven benefits of inhibiting LIF/LIFR and subsequent JAK/STAT signaling and other downstream targets like AKT and ERK in PCa cells along with inhibition of CSC population and maintenance markers. These findings provoked us to investigate the synergistic effect of EC914 with DTX in preclinical settings.

Figure 6A:
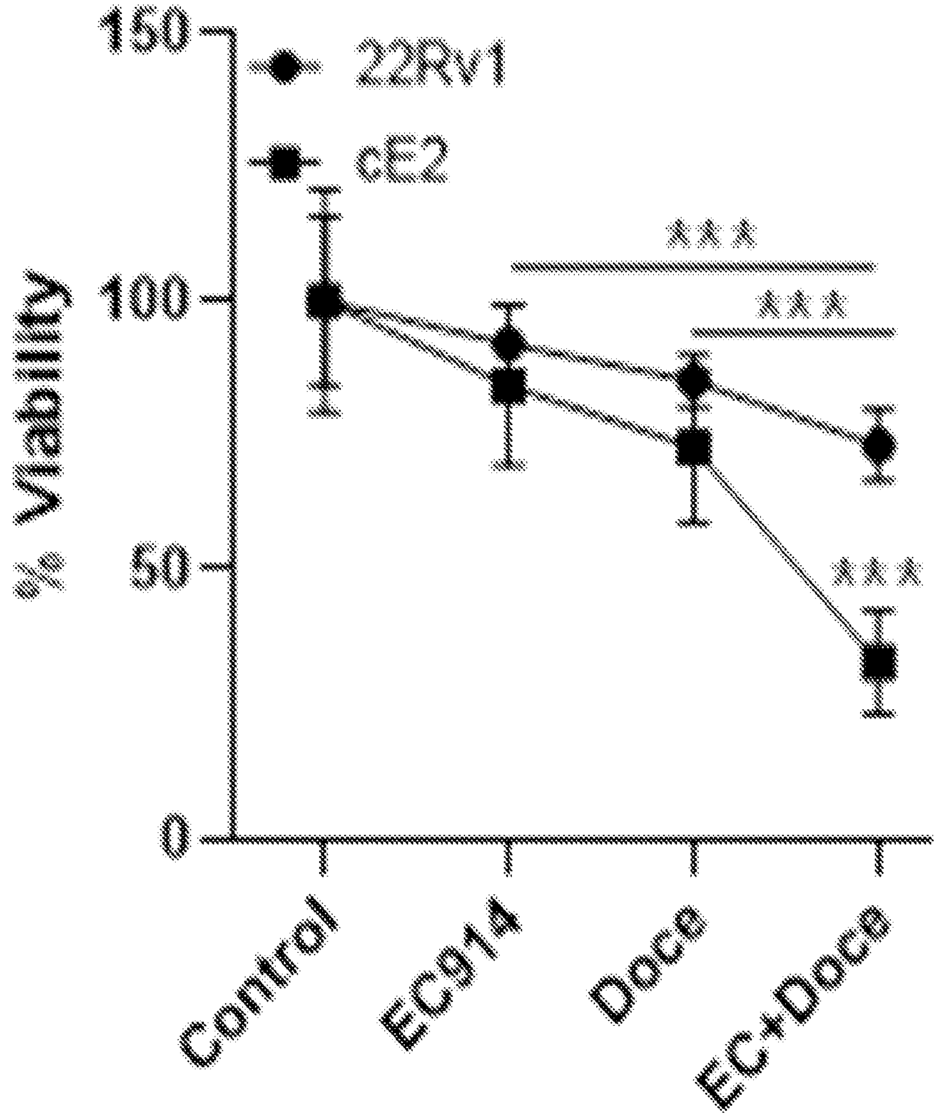
FIG. 6A depicts a line graph showing significant decline in the viability of murine and human PCa cells upon treatment with EC914 and/or Docetaxel.
Figure 6B:
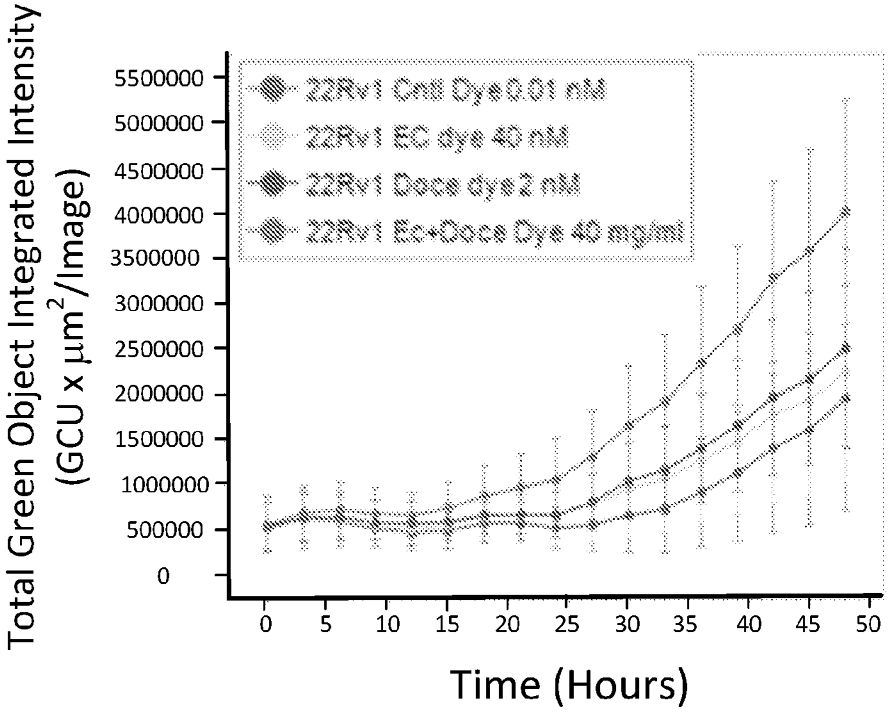
FIG. 6B depicts a cytotoxicity curve for 22Rv1 cells analyzed in an Incucyte® Cytotox assay.

As shown in FIG. 6, EC914 decreases viability and increases cytotoxicity of Docetaxel in PCa. FIG. 6A depicts a line graph showing significant decline in the viability of murine and human PCa cells upon treatment with EC914 and/or Docetaxel. FIG. 6B shows a cytotoxicity curve for 22Rv1 cells analyzed in an Incucyte® Cytotox assay.

Figure 7A:
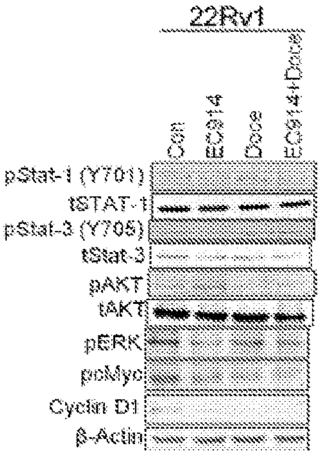
FIG. 7A depicts a western blot analysis of the effect of EC914 and docetaxel, alone or in combination, on STAT1, STAT3, AKT, ERK, Myc, and tCyclinD1 proteins.
Figure 7B:
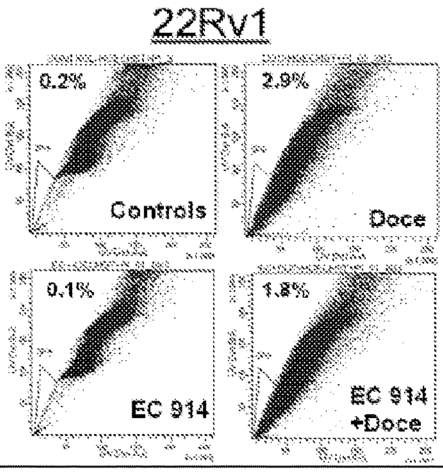
FIG. 7B depicts an FACS analysis showing the effect of EC914 and docetaxel, alone or in combination, on cancer stem cells.
Figure 7C:
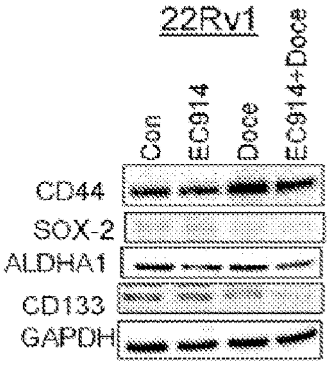
FIG. 7C depicts a western blot analysis on key CSC marker expression (MDR1, CD44, Sox2, ALDH1, and CD133) of PCa.

FIG. 7 shows that treatment with EC914 reduces cancer stem cells (CSC) and CSC proteins. In this study, the cellular signaling disrupted upon EC 914 treatment was analyzed. This study shows that that EC914 alone and in combination with DTX decreased the phosphorylation of STAT1 and STAT3 along with its stream targets phosphorylation of AKT, ERK, Myc, and tCyclinD1 proteins, while no change in respective total proteins expression (FIG. 7A). In light of CSC's importance in supporting metastatic re-colonization, exposure of EC914 alone and in combination with DTX resulted in ~40-50% reduction in SP compared to no drug or DTX treated control cells by FACS analysis (FIG. 7B). Consistently, FIG. 7C shows that EC914 specifically decreases key CSC marker expression (MDR1, CD44, Sox2, ALDH1, and CD133) of PCa. Thus, cancer stemness enrichment upon DTX treatment might be abolished by LIF/LIFR signaling disruption through EC914 inhibitor.

Figure 8:
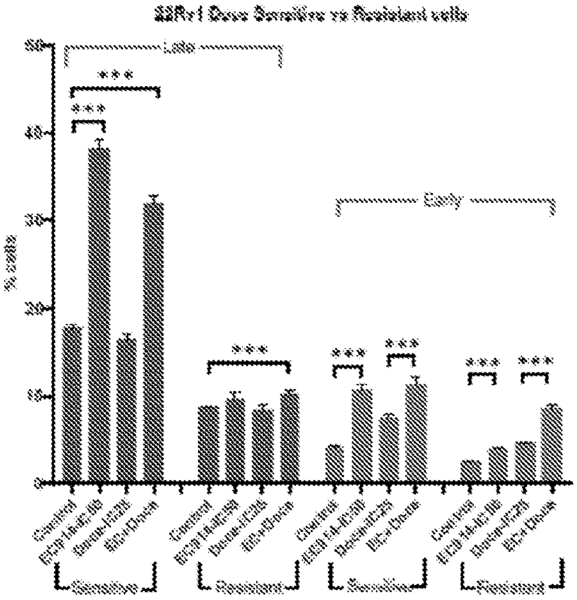
FIG. 8 depicts a graph showing that the combination of docetaxel and EC914 induces apoptosis in docetaxel sensitive and resistant 22Rv1 prostate cancer cells.

FIG. 8 depicts a graph showing that the combination of docetaxel and EC914 induces apoptosis in docetaxel sensitive and resistant 22Rv1 prostate cancer cells.

Figure 9:
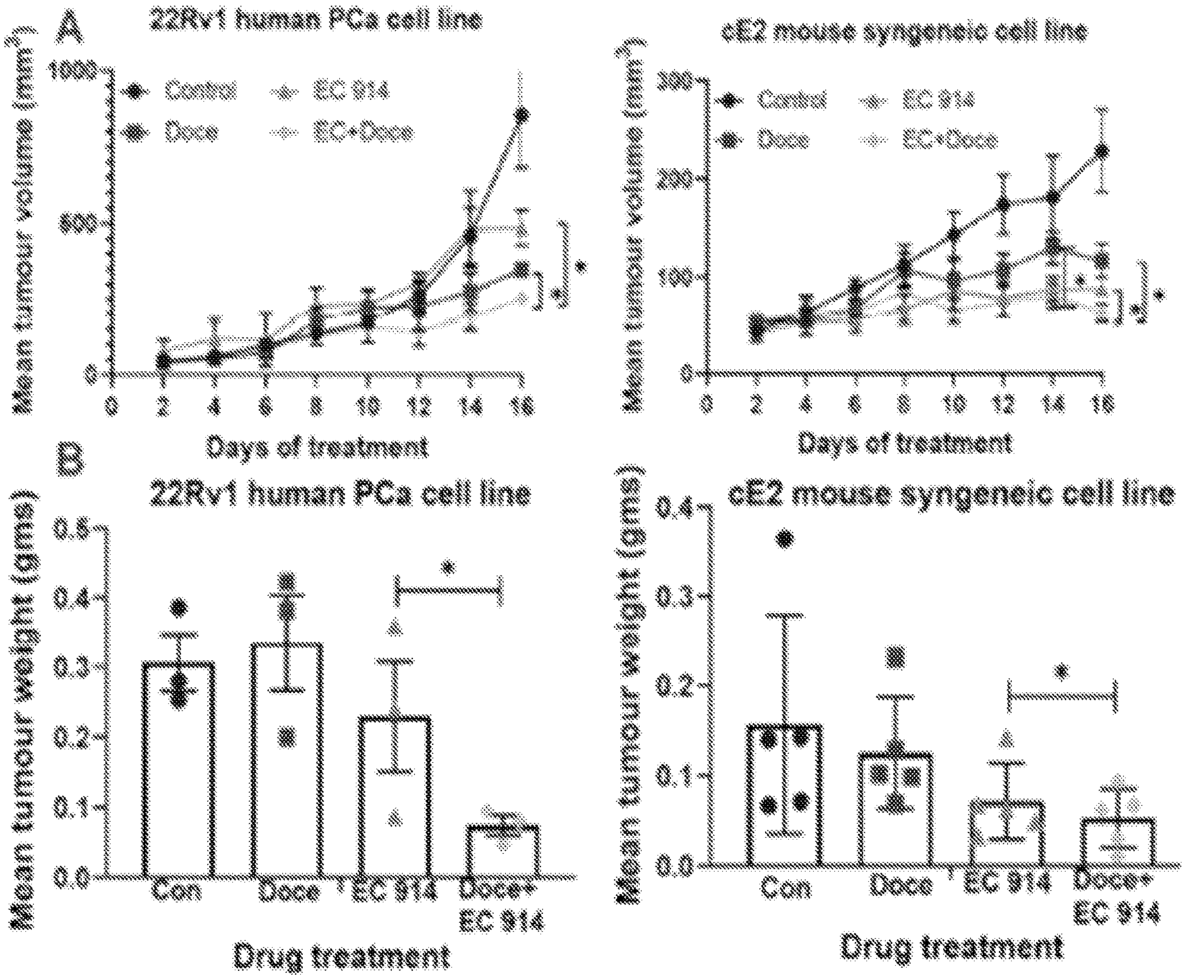
FIG. 9 depicts data showing that EC914 alone or in combination with docetaxel inhibit tumor growth in prostate cancer models in vivo.

22Rv1 and cE2 mouse syngeneic cells were subcutaneously implanted in athymic nude mice (0.75x106/mice). Two weeks after post-implantation, mice were randomized into four groups. Group 1 mice received saline, whereas group 2 and group 3 mice received EC 914 (every alternative day) or DTX (once in 3 days) alone. Finally, group 4 mice were administered with both EC 914 and DTX. FIG. 9 depicts data showing that EC914 alone or in combination with docetaxel inhibit tumor growth in prostate cancer models in vivo. As shown in FIG. 9, the in vivo xenograft tumors treated with EC914 and DTX resulted in significantly more tumor shrinkage and reduced tumor growth than either of the agents alone. Subsequently, reduced xenograft tumor growth upon drug treatment decreased human and mouse xenograft tumor weights, as measured during necropsy. Based on this rationale, it is believed that LIFR is overexpressed in response to DTX treatment and induces resistance, and enriches the CSC population in metastatic CRPC. This data suggests that EC 914 synergizes with DTX to enhance cell killing and reduce the colony growth.

Based on this preliminary data, it is believed that the activation of LIF/LIFR signaling promotes docetaxel resistance by enriching CSC and suppressing the LIF/LIFR axis. Treatment with EC914 abrogates Jak/STAT signaling and cancer sternness to reverse and overcome DTX-mediated chemoresistance in metastatic CRPC.

I

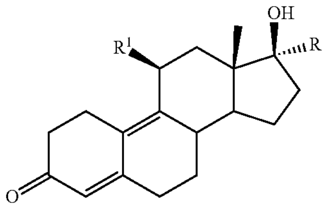

Compounds having general formula I are synthesized as outlined in the Scheme 1.

Scheme 1.

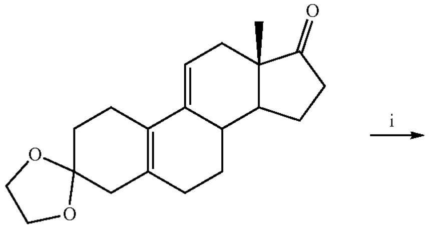

1

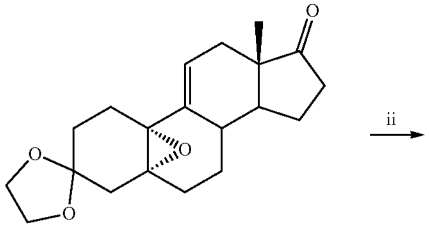

2

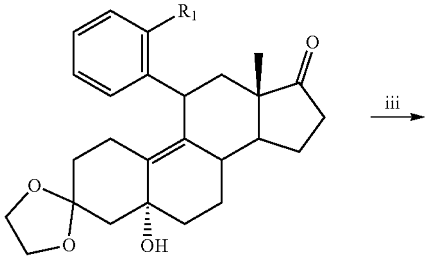

3

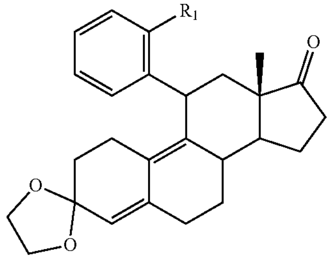

4

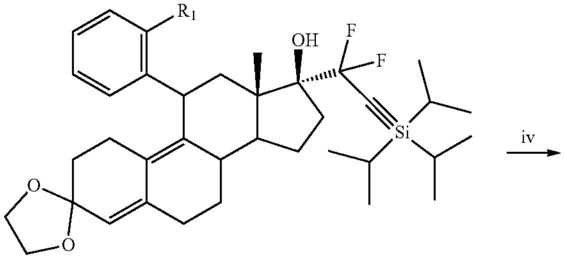

5

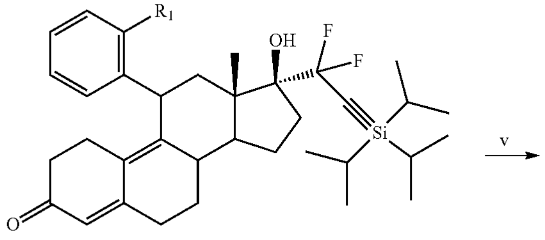

6

-continued

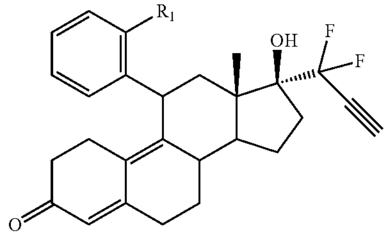

i) Epoxidation; ii) Grignard reaction; ii) $Ac_2O$, DMAP, Py; iii) 3-bromo-3,3-difluoro-1-triisopropylsilylpropyne, n-BuLi, THF; iv) 4N, HCl; v) TBAF, THF.

In an embodiment, a chemical intermediate for the synthesis of compounds having the structures (I)-(IV) has the structure (V):

(V)

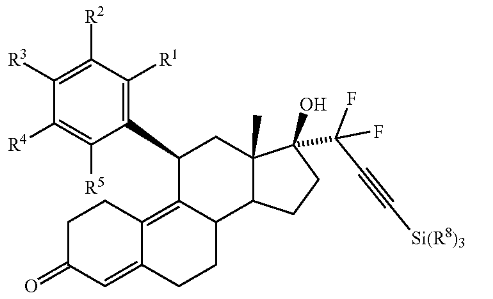

$R^1$, $R^2$, $R^3$, $R^4$, and $R^5$ are, independently, H, D, halogen, CN, OH, aryl, alkyl, cycloalkyl, heteroaryl, $—O(CH_2)_n—NR^6R^7$, $—O(CH_2)_n—OR^6$, $—O(CH_2)_n—SR^6$, $—O(CH_2)_n—S(O)R^6$, $—O(CH_2)_n—SO_2R^6$, $—O(CH_2)_n—COOR^6$, $—O(CH_2)_n—CONR^6R^7$, $—O(CH_2)_n—N(R^6)COR^7$, $—OCONR^6R^7$, $—N(R^6)CO_2R^7$, $—OR^6$, $—NR^6R^7$, $—CH(R^6)—OR^7$, $—CONR^6R^7$, —OD, or $—CD_3$;

n=1 to 4; and $R^6$ and $R^7$ are, independently, H, alkyl, cycloalkyl, or $CD_3$;

wherein at least one of $R^1$, $R^2$, $R^4$, or $R^5$ is not hydrogen.

EXPERIMENTAL

All the reagents and solvents were analytical grade and used without further purification. Thin-layer chromatography (TLC) analyses were carried out on silica gel GF (Analtech) glass plates (2.5 cm×10 cm with 250 μM layer and pre-scored) and visualized by UV light (254 nm). Flash column chromatography was performed on 32-64 μM silica gel obtained from EM Science, Gibbstown, New Jersey. Melting points were determined on an Electro thermal MEL-TEMP apparatus and are uncorrected. Nuclear magnetic resonance spectra were recorded on a Bruker ARX (300 MHz) spectrometer as deuterochloroform ($CDCl_3$) solutions using tetramethylsilane (TMS) as an internal standard (δ=0) unless noted otherwise. IR spectra were recorded on an Avatar spectrophotometer 370 FT-IR.

Scheme 1

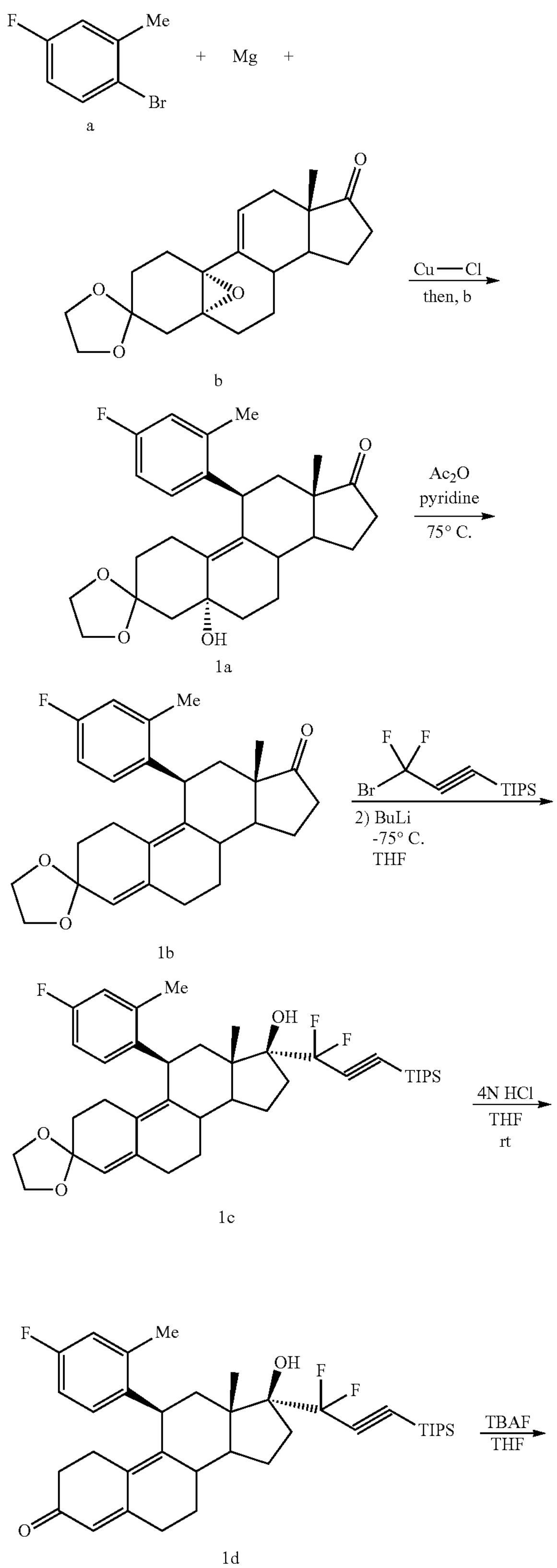

-continued

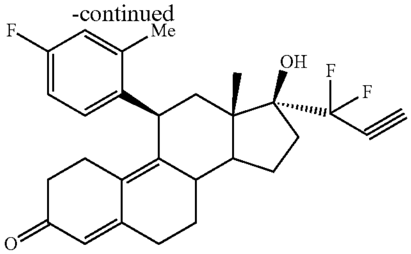

1

General Method 1 (5 steps):

2-Bromo-5-fluorotoluene (10.0 g, ~10 mL, 52.9 mmol, 2.5 eq) was dissolved in THF (20 mL), and 3 mL of this solution about 1 g of the bromide was taken in an oven dried flask fitted with stirrer and nitrogen. To this solution, magnesium (2.0 g, 82.3 mmol, 3.9 eq) was added and followed by the addition of 1,2-dibromoethane (0.04 mL). The mixture was heated in a preheated oil bath set a 55° C. The reaction with magnesium became vigorous in few minutes, and the rest of the bromide solution was then added dropwise with help of a syringe in such a rate that the reaction was maintained. After the completion of the addition, it was heated for an additional hour. The reaction was cooled to −10° C., diluted with THF (20 mL), and CuCl (0.21 g, 2.12 mmol, 0.1 eq) was added and stirred for 5 minutes. To this solution, the solution of steroid epoxide (7.0 g, 21.2 mmol, 1 eq in 40 mL THF) was added over 15 minutes to keep the temperature under 0° C. The reaction was stirred for an additional hour at this temperature. The TLC showed complete consumption of the epoxide. The reaction was quenched with sat. aq. $NH_4Cl$ (40 mL), diluted with water (5 mL) and stirred for 75 minutes under air to oxidize the Cu-I to Cu-II, the color of the aqueous solution turned blue. $Na_2SO_4$ (5 g) was added, extracted with ethyl acetate (2×85 mL), the combined organic layer was dried over $Na_2SO_4$, filtered, and concentrated to a solid crystalline crude (10.0 g).

The crude was dissolved in DCM (85 mL) and heated to reflux under stirring to reduce the volume to 65 mL. To this solution under reflux was added hexane (65 mL) dropwise. The solution was reduced to 65 mL and the product was started to crystallize. The heating was stop and the solution was cooled to room temperature, it sat for 1 hour and the crystals were collected on Buchner funnel fitted with filter paper. The crystals were dried under vacuum to afford the off-white product 1a (6.0 g, 64%). The mother liquor was concentrated and was purified by basic alumina chromatography on a 100 g column using 0-60% ethyl acetate in hexanes as eluent to afford the white crystalline product 1a (3.0 g, 32%) (total yield 96%).

The compound 1a (9.0 g, 20.4 mmol, 1.0 eq) was dissolved in pyridine (30 mL) under stirring under nitrogen. Acetic anhydride (9.7 mL, 102 mmol, 5.0 eq) and DMAP (0.30 g, 2.5 mmol, 0.12 eq) were added and the reaction was heated at 75° C. for 5.5 hours. The reaction turned dark brown. It was diluted with heptane (2×100 mL) and concentrated under rotavap. The crude was purified by basic alumina chromatography using 0-40% ethyl acetate in hexanes to afford the white crystals 1b (5.80 g).

The compound 1b (5.80 g, 13.7 mml, 1 eq) and 3-bromo-3,3-difluoro-1-TIPS-propyne (12.7 mL, 41.2 mmol, 3.0 eq) were dissolved in THF (175 mL) in an oven dried 3-necked 500 mL RB flask fitted with thermometer, stirred bar and nitrogen. It was cooled to −78° C. n-BuLi (2.5 M in hexane, 16.5 mL, 41.2 mmol, 3.0 eq) was added dropwise over 40 minutes to maintain the reaction temperature under below −74° C. The dark brown reaction solution was further stirred for 1 hour at −76° C. TLC showed most of the starting material consumed. The reaction was quenched with sat. aq. $NH_4Cl$ (50 mL), and 10% aq. $Na_2SO_4$ (20 mL), extracted with ethyl acetate (2×50 mL), the combined organic layer was washed with brine (50 mL), dried over $Na_2SO_4$, filtered, concentrated and the crude 1c was used without purification.

The compound 1c (crude, 13.7 mmol, 1 eq) was dissolved in THF (50 mL) at rt under stirring, and aq. HCl (4M, 50 mL, 100 mmol, 7.3 eq) was added. The resulting pale solution was stirred for 75 minutes at rt. It was diluted with water (10 mL), extracted with DCM (2×50 mL), the combined organic was washed with brine (30 mL), dried over $Na_2SO_4$, filtered, concentrated and the crude was purified by silica gel chromatography on a 100 g column using 0-20% ethyl acetate in hexanes to afford the beige solid product 1d (5.50 g, 65.7% over 2 steps).

The compound 1d (5.5 g, 1 eq) was dissolved in THE (50 mL) under stirring under nitrogen and this solution was cooled under ice bath. TBAF·3H2O (2.84 g, 1 eq) was added, the reaction solution turned dark brown, it was stirred at this temperature for 5 minutes, and the TLC showed complete conversion. The reaction was quenched with sat. aq. $NH_4Cl$ (30 mL), the crude product was extracted with DCM (2×30 mL), the combined organic was dried over $Na_2SO_4$, filtered, concentrated and the crude was purified by silica gel chromatography using 0-50% ethyl acetate in hexanes to afford the beige product 1 (3.2 g, 78.2%). $^1H$ NMR ($CDCl_3$, 300 MHz) δ 0.81 (s, 3H, H-18), 2.37 (s, 3H), 2.89 (t, J=5.4 Hz, 1H), 4.39 (d, J=8.9 Hz, H-11), 5.72 (s, 1H, H-4), 6.74 (dt, J=5.6, 8.1 Hz, 1H, H—Ar), 8.86 (dd, J=2.7, 9.5 Hz, 1H, H—Ar), 6.97 (dd, J=5.6, 8.5 Hz, 1H, H—Ar).

2

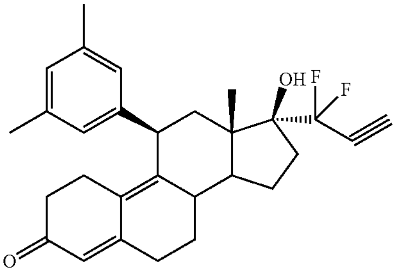

The compound 2 was synthesized according to the procedure described in general method 1, and the compound 2 as pale foam (0.64 g). $^1H$ NMR ($CDCl_3$, 300 MHz) δ 0.63 (s, 3H, H-18), 2.27 (s, 6H, 3,5-diMe-aryl), 2.91 (t, J=6.0 Hz, 1H, H-alkyne), 4.36 (d, J=6.0 Hz, H-11), 5.77 (s, H-4), 6.75 (s, 2H, H—Ar), 5.79 (s, 1H, H—Ar), $^{13}C$ NMR ($CDCl_3$, 75 MHz) δ 16.6 (C-18), 21.6 (Ar-di$\underline{C}H_3$), 24.3 (Ar—$\underline{C}H_3$), 25.8, 27.7, 31.0, 33.7, 36.8, 38.7, 39.2, 40.5, 47.7, 51.2, 51.2, 85.9 (t, J=26.2 Hz, ($\underline{C}F_2CC$)), 109.1, 109.9, 112.8, 116.0, 119.2, 123.0, 124.6, 124.6, 127.4, 127.4, 129.5, 137.9, 144.3, 145.2, 156.5 (C-9), 199.6.

Equation 1

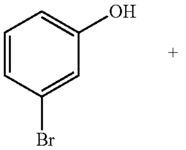

-continued

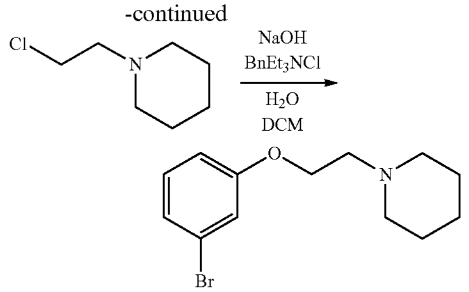

c

3-Bromophenol (7.75 g, 44.8 mmol), N-(2-chloroethyl)-piperdine (8.9 g, 48.3 mmol), benzyl-triethylammoniom chloride (0.75 g) and sodium hydroxide (13 mL of 30% in water, 2.2 eq.) in DCM (45 mL) were stirred at ambient temperature. The bromide c was prepared according to procedure in the reference as a clear oil (12.77 g, 100%) (Ref.: *Org. Proc. Res. & Development* 2002, 6, 20-27).

3

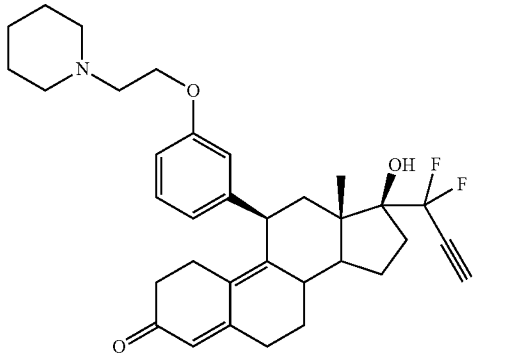

The compound 3 was synthesized according to the procedure described in general method 1. The bromide c (7.7 g, 27.1 mmol) was reacted with magnesium (0.99 g, 40.8 mmol) in the presence of iodine (1 crystal) and 1,2-dibromoethane (50 uL) in THF (55 mL) at 65-70° C. for 1 hour, which then reacted with the epoxide b (3.5 g, 10.6 mmol) in the presence of CuCl (0.22 g, 2.22 mmol). After purification, the compound 3a was afforded as white foam (4.9 g, 86%)).

The compound 3a (4.9 g, 9.1 mmol) was treated with acetic anhydride (3.5 mL, 36.6 mmol) and 4-dimethylaminopyridine (335 mg, 2.7 mmol) at 65-70° C. for 16 hours. The crude was concentrated and purified with basic alumina column with 0-50% acetone spike with 1.5% ammonia and hexanes to afford the pale foam 3b (3.9 g, 83%).

The compound 3b (1.7 g, 3.3 mmol) was treated with n-BuLi (2.3 M, 5.7 mL, 13.1 mmol) in THF (50 mL) at −78° C. in the presence of the bromodifluoropropargyl-1-TIPS (4.0 mL, 13.1 mmol), and the reaction was stirred for 3 hours at −78° C. The NMR showed only 50% conversion after purification with basic alumina column with 0-50% acetone spike with 1.5% ammonia and hexanes, and the starting material and the product were not separated. This mixture was then treated with aq. sulfuric acid in THF to afford the 3d (0.41 g).

The 3d was treated with TBAF to remove the TIPS group to afford the compound 3 (0.23 g) as white foam. FT IR (ATR, $cm^{-1}$): 3297, 2935, 2855, 2125, 1646, 1596. $^1H$ NMR ($CDCl_3$, 300 MHz) δ 0.63 (s, 3H, H-18), 1.02 (t, J=7.1 Hz, 2H), 2.75 (t, J=6.2 Hz, 2H, Ar—$C\underline{H}_3$), 2.90 (t, J=5.3 Hz, 1H, acetylenic hydrogen), 4.39 (d, J=7.0 Hz, 1H, H-11), 5.77 (s, 1H, H-4), 6.74 (m, 3H, H—Ar), 7.17 (t, J=7.9 Hz, 1H, H—Ar). $^{13}C$ NMR ($CDCl_3$, 75 MHz) δ 11.28, 16.4, 24.1, 24.2, 25.5, 25.7, 27.6, 37.0, 33.5, 36.7, 38.6, 39.1, 40.6, 46.0, 47.6, 51.1, 55.0, 57.89, 65.7, 76.1, 85.7 (t, J=24.7 Hz, ($\underline{C}F_2CC$)), 111.1, 114.1, 119.2, 122.9 (C—Ar), 129.3, 129.6, 144.9, 146.1, 156.5, 159.60, 199.5 (C-3).

Equation 2

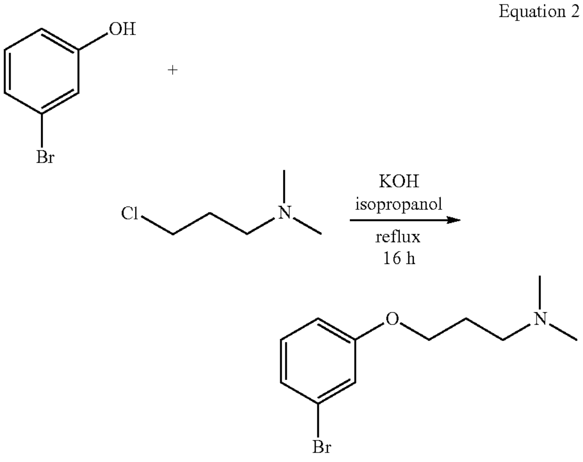

d

The synthesis of amino-propyl piece d was tried with the chloro-compound 2b (3.7 g, 30.4 mmol), 3-bromophenol (7.5 g, 43.3 mmol, 1.4 eq) and KOH (2.6 g, 1.4 eq) in isopropanol (50 mL) under vigorous stirring at reflux for 16 to afford the compound d (6.4 g, 81%) (Ref: *J. Combinatorial Chemistry* 2003, 5, 606-609).

4

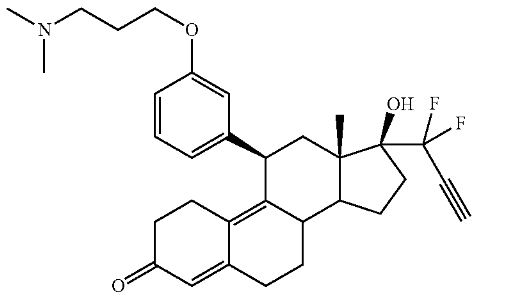

The compound 4 was synthesized according to the procedure described in general method 1. The bromide d (6.4 g, 24.8 mmol, 2 eq) was reacted with magnesium (0.75 g, 31 mmol, 2.5 eq) in the presence of iodine (1 crystal) and 1,2-dibromoethane (0.05 mL) in THF (40 mL) at 55° C. for 75 minutes. The reaction was cooled to −10° C. and reacted with the epoxide b (4.1 g, 12.4 mmol, 1 eq) in the presence of CuCl (0.165 g, 1.7 eq). It was stirred for 3 hours at rt after slow warming to ambient temperature and quenched with sat. aq. $NH_4Cl$ (50 mL). After purification, the compound 4a was afforded as white foam (4.38 g).

The compound 4a (4.38 g) was treated under dehydration conditions as described in general procedure 1 to afford the pale foam 4b (3.4 g) after purification with basic alumina chromatography with 0-50% acetone in hexanes, hexanes contained 1.0% triethylamine.

The ketone 4b (1.8 g) was subjected to 17-addition as described in general procedure 1, and after purification it yielded the compound 4c as white foam (0.39 g).

The ketal was removed as described in general procedure 1 to afford the dienone 4d (0.15 g) after purification.

The TIPS group was removed with TBAF as described in general procedure 1 to afford 4 (0.10 g) as white foam. FT IR (ATR, $cm^{-1}$): 3291, 2947, 2868, 2126, 1647, 1596. $^1H$ NMR ($CDCl_3$, 300 MHz) δ 0.63 (s, 3H, H-18), 2.26 (s, 6H), 2.90 (t, J=5.2 Hz, 1H, acetylenic-H), 3.98 (t, J=6.2 Hz, 2H), 4.38 (d, J=6.4 Hz, 1H, H-11), 5.76 (s, 1H, H-4), 6.70 (m, 3H, H—Ar), 7.15 (t, J=7.9 Hz, 1H, H—Ar). $^{13}C$ NMR ($CDCl_3$, 75 MHz) δ 16.4, 24.24, 24.29, 25.5, 25.7, 27.35, 27.65, 29.2, 31.0, 33.6.0, 36.7, 38.6, 39.2, 40.5, 45.30, 47.7, 51.1, 56.3, 66.0, 76.5, 76.8, 85.7 (t, J=24.7 Hz, ($CF_2CC$)), 111.1, 114.0, 119.1, 123.0, 129.4, 129.7, 144.8, 146.0, 156.4, 159.1, 199.4 (C-3).

Equation 3

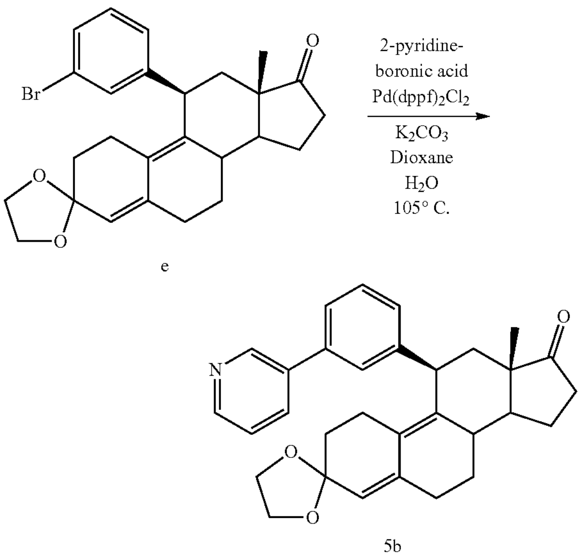

e

5b

The bromide 17 (1.0 g, 2.1 mmol, 1 eq) was reacted with 2-pyridine boronic acid (0.77 g, 6.3 mmol, 3 eq) in the presence of $Pd(dppf)_2Cl_2$ (0.15 g, 0.21 mmol, 0.1 eq) and $K_2CO_3$ (0.87 g, 6.3 mmol, 3 eq) under reflux for 5 h. After basic alumina chromatography with 0-80% ethyl acetate in hexanes, the biaryl 5b was yielded as pale foam (0.59 g).

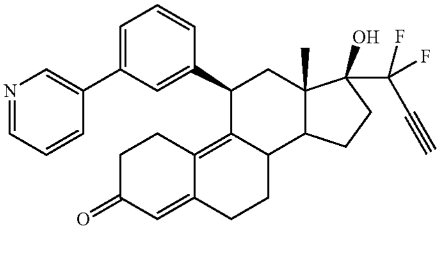

The ketone 5b (0.5 g) was subjected to 17-addition conditions as described in general procedure 1 to synthesize the alcohol 5c.

The compound 5c was treated with sulfuric acid as described in general procedure 1 to afford the ketone 5d (0.37 g) as beige solid.

The removal of the TIPS group was accomplished by TBAF, and purification under silica chromatography with 0-50% acetone in hexanes as described in general procedure 1 yielded the compound 5 (EC905) (0.24 g) as beige solid. FT IR (ATR, $cm^{-1}$): 3290, 2950, 2871, 2126, 1651, 1598. $^1H$ NMR ($CDCl_3$, 300 MHz) δ 0.65 (s, 3H, H-18), 2.91 (t, J=5.4 Hz, 1H, acetylenic-H), 4.52 (d, J=6.8 Hz, 1H, H-11), 5.79 (s, 1H, H-4), 7.20 (m, 1H, H—Ar), 7.37 (m, 4H), 7.82 (m, 1H), 8.59 (dd, J=1.5, 4.7 Hz, 1H), 8.79 (d, J=1.9 Hz, 1H).

Scheme 2

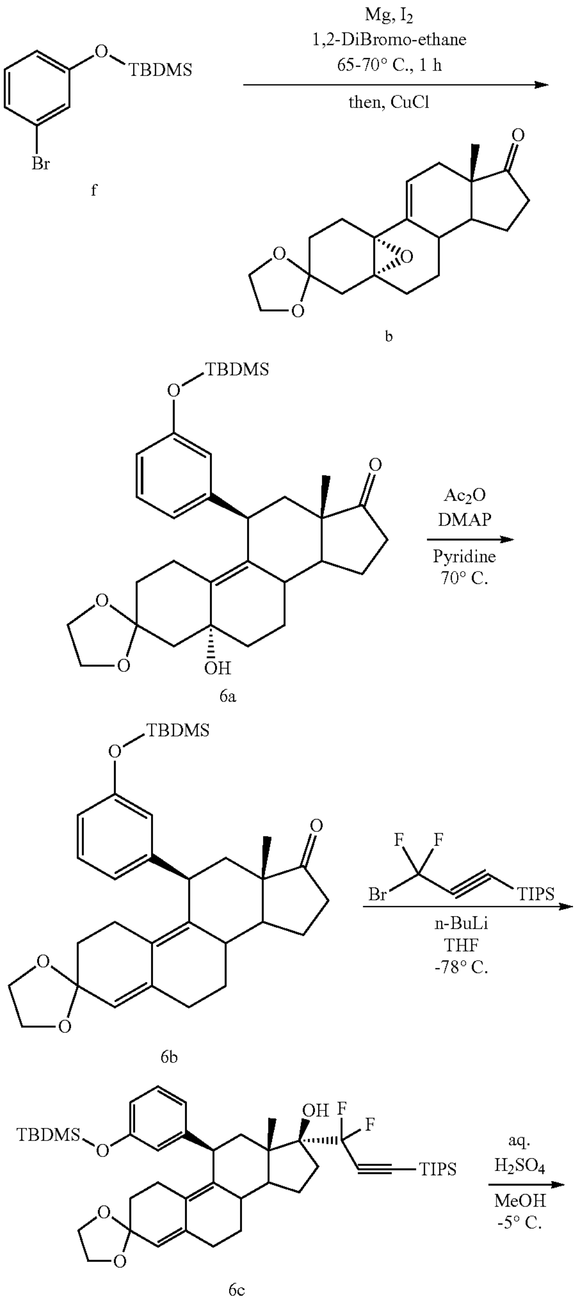

f b

6a

6b

6c

-continued

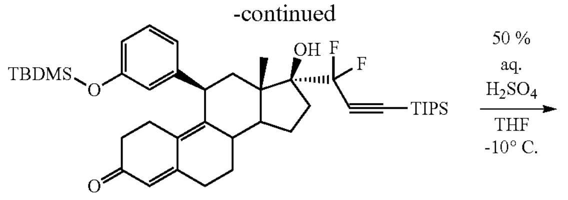

6e

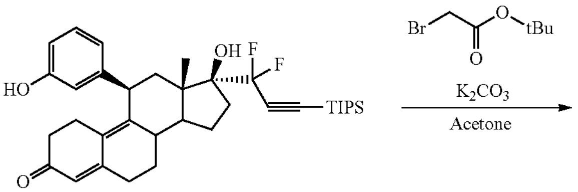

6f

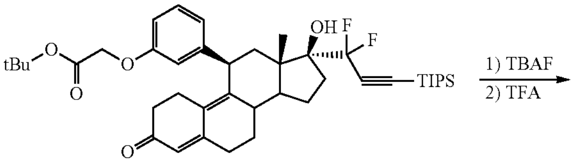

6d

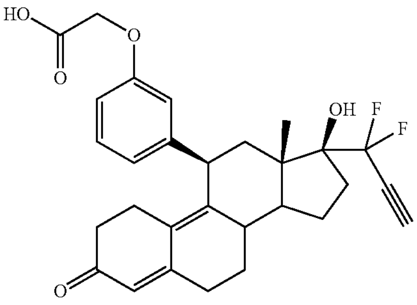

6

The bromide f (6.4 g, 2 eq) was reacted with magnesium (2.5 eq) in the presence of iodine and 1,2-dibromoethane, which then reacted with the epoxide b (3.5 g) in the presence of CuCl as described in general procedure 1. After purification under silica chromatography with 0-30% acetone in hexanes, the compound 6a was afforded as white foam (4.8 g).

The alcohol 6a (4.8 g) was subjected to dehydration conditions as described in general procedure 1 to afford the diene 6b (2.2 g) as white foam after basic alumina chromatography with 0-30% acetone in hexanes.

The 17-ketone 6b (2.2 g) was reacted with the 3,3,3-difluorobromo-propygyl-TIPS in the presence of $^n$BuLi according to procedure as described in general procedure 1 to afford the alcohol 6c. The alcohol 6c was used as crude for the next step.

The alcohol 6c was treated 50% aq sulfuric acid in Methanol at −4° C. for 4h. The crude was purified by silica gel chromatography using 0-30% acetone in hexanes to afford the ketone 6e (1.95 g). The TBS-ether 6e was cleaved under 50% aq sulfuric acid (10 eq) in THF at rt for 4 h. The reaction was completed. The crude was purified by silica gel chromatography using 0-60% ethyl acetate in hexanes to afford the phenol 6f (0.95 g) as beige solid.

The phenol 6f (0.95 g) was then treated t-butyl bromoacetate (1.5 eq) in the presence of potassium carbonate (2 eq) in acetone (10 mL) at rt for 20 h. It was diluted with water and ethyl acetate. The organic layer was separated, dried over $Na_2SO_4$, filtered, concentrated, and the cruse was purified by silica gel chromatography using 0-30% ethyl acetate in hexanes to afford the ester 6d (0.85 g) as clear foam.

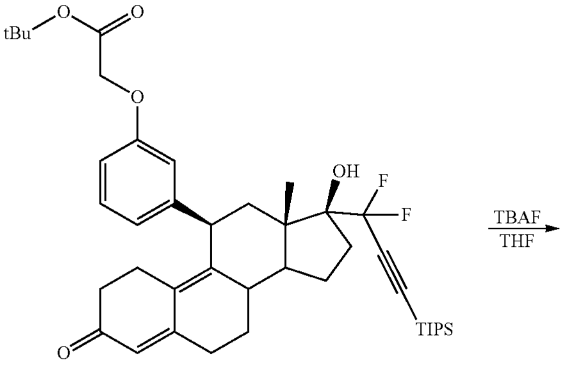

6d

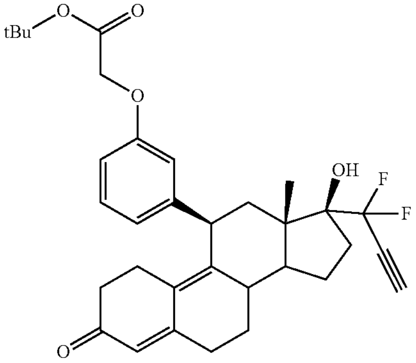

7

The product 7 was also prepared from 6d according to procedure as described in general procedure 1. $^1$H NMR ($CDCl_3$, 300 MHz) δ 0.62 (s, 3H, H-18), 1.47 (s, 9H), 2.90 (t, J=5.4 Hz, 1H, acetylenic-H), 4.39 (d, J=6.7 Hz, 1H, H-11), 4.48 (s, 2H), 5.76 (s, 1H, H-4), 6.63 (dd, J=2.3, 8.1 Hz, 1H, H—Ar) 6.79 (m, 2H, H—Ar), 7.18 (t, J=7.9 Hz, 1H, H—Ar).

The product 6 was prepared from by treating the product 7 (0.50 g) with TFA (2 mL) in DCM (1.5 mL) at ambient temperature under for 2 hours. The reaction was concentrated, and the crude was purified by silica gel chromatography.

Scheme 3

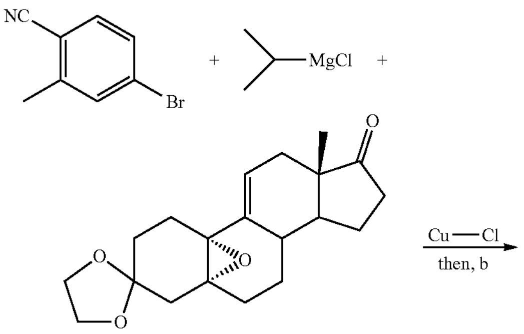

b

-continued

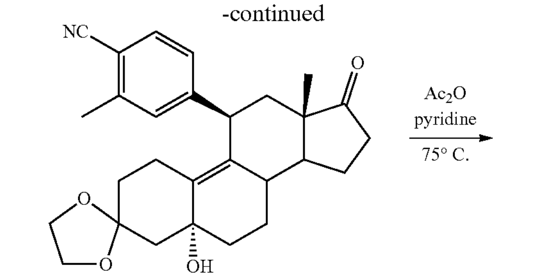

8a

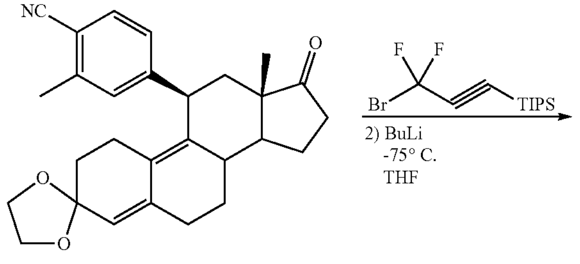

8b

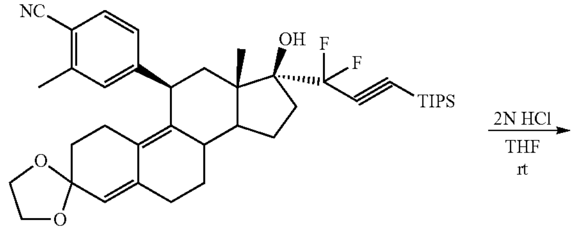

8c

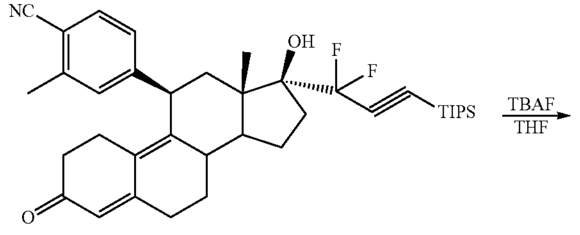

8d

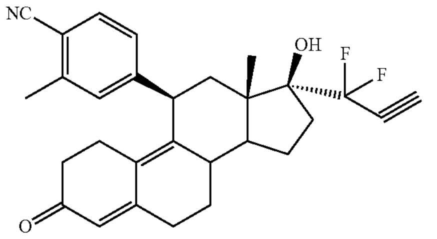

8

General Method 2:

Synthesis of compound 8 according to scheme 3. 4-Bromo-2-methyl-benzonitrile (5.0 g, 25.5 mmol, 2.5 eq) was dissolved in THF (50 mL) in an oven dried flask fitted with stirrer, thermocouple, and nitrogen. The solution was cooled to −15° C., and isopropyl-magnesium chloride lithium chloride in THF (1.3 M, 19.6 mL, 25.5 mmol, 2.5 eq) was added dropwise keeping the internal temperature below −5° C. during the addition. The pale reaction solution was stirred at −2 to 0° C. for 3 hours. CuCl (30 mg) was added at 0° C., followed by the addition of the epoxide b (solid, 3.4 g, 10.3 mmol, 1.0 eq). The temperature of reaction went as high as 13° C. and then started falling to 5° C. The reaction turned dark brown, and it was stirred for 40 minutes at this temperature. The TLC showed complete consumption of the epoxide. The reaction was quenched with sat. aq. $NH_4Cl$ (25 mL), diluted with water (100 mL), extracted with ethyl acetate (2×50 mL), the combined organic layer was washed with brine (100 mL), dried over $Na_2SO_4$, filtered, and concentrated. The crude was purified by silica chromatography on a 100 g column using 0-20% acetone in DCM as eluent to afford the white foam product 8a (3.6 g, 78%).

The compound 8a (3.5 g, 7.8 mmol, 1.0 eq) was dissolved in pyridine (20 mL) under stirring under nitrogen. Acetic anhydride (3.7 mL, 39.1 mmol, 5.0 eq) and DMAP (0.191 g, 1.56 mmol, 0.2 eq) were added and the reaction was heated at 75° C. for 17 hours. The reaction turned dark brown. It was diluted with heptane (2×125 mL) and concentrated under rotavap. The crude was purified basic alumina chromatography on a 100 g column with 0-10% acetone in DCM to afford the white foam product 8b (3.16 g, 94%).

The compound 8b (3.16 g, 7.36 mml, 1 eq) and 3-bromo-3,3-difluoro-1-TIPS-propyne (5.0 mL, 16.2 mmol, 2.2 eq) were dissolved in THF (90 mL) in an oven dried 3-necked 250 mL V-shaped flask fitted with thermometer, stirred bar and nitrogen. It was cooled to −78° C. n-BuLi (1.9 M in hexane, 8.52 mL, 16.2 mmol, 2.2 eq) was added dropwise over 35 minutes to maintain the reaction temperature under −74° C. The dark brown reaction solution was further stirred for 2 hours at −76° C. TLC showed most of the starting material consumed. The reaction was quenched with sat. aq. $NH_4Cl$ (25 mL), diluted the water (25 mL) and brine (100 mL), extracted with ethyl acetate (2×50 mL), the combined organic layer was dried over $Na_2SO_4$, filtered, concentrated and the crude was purified by basic alumina chromatography using 0-80% ethyl acetate in hexanes to afford the product 8c as brown foam (3.30 g, 67%).

The compound 8c (3.30 g, 1 eq) was dissolved in THF (33 mL) at rt under stirring, and aq. HCl (2M, 12.6 mL, 5 eq) was added. The resulting brown solution was stirred for 19 hours at rt. It was diluted with water (30 mL), extracted with DCM (2×45 mL), the combined organic was dried over $Na_2SO_4$, filtered, concentrated and the crude was purified by silica gel chromatography using 0-60% ethyl acetate in hexanes to afford the beige foam product 8d (1.84 g, 60%).

The compound 8d (1.83 g, 1 eq) was dissolved in THF (20 mL) under stirring under nitrogen and this solution was cooled ice bath. TBAF·3H2O (0.935 g, 1 eq) was added, the reaction solution turned dark brown, it was stirred at this temperature for 5 minutes, and the TLC showed complete conversion. The reaction was quenched with sat. aq. $NH_4Cl$ (30 mL), the crude product was extracted with DCM (2×45 mL), the combined organic was dried over $Na_2SO_4$, filtered, concentrated and the crude was purified by silica gel chromatography using 0-60% ethyl acetate in hexanes to afford the beige foam product 8 (1.18 g, 85%). $^1H$ NMR ($CDCl_3$, 300 MHz) δ 0.57 (s, 3H, H-18), 2.51 (s, 3H, $CH_3$), 2.91 (t, J=6 Hz, 1H, acetylenic-H), 4.41 (d, J=6 Hz, 1H, H-11), 5.79 (s, 1H, H-4), 7.06 (d, J=9 Hz, 1H), 7.15 (s, 1H), 7.49 (d, J=9 Hz, 1H).

9

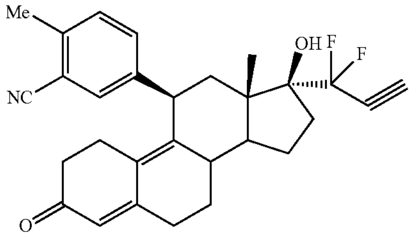

The product 9 was prepared according to procedure described in general method. 2. 5-Bromo-2-methyl-benzonitrile (5.0 g, 25.5 mmol, 2.5 eq) was dissolved in THE (50 mL) in an oven dried flask fitted with stirrer, thermocouple, and nitrogen. The solution was cooled to −15° C., and isopropyl-magnesium chloride lithium chloride in THF (1.3 M, 19.6 mL, 25.5 mmol, 2.5 eq) was added dropwise keeping the internal temperature below −5° C. during the addition. The pale reaction solution was stirred at −2 to 0° C. for 3 hours. CuCl (30 mg) was added at 0° C., followed by the addition of the epoxide b (solid, 3.4 g, 10.3 mmol, 1.0 eq). The temperature of reaction went as high as 10° C. and then started falling to 5° C. The reaction turned dark brown, and it was stirred for 40 minutes at this temperature. The TLC showed complete consumption of the epoxide. The reaction was quenched with sat. aq. $NH_4Cl$ (25 mL), diluted with 10% aq. $Na_2SO_4$ (50 mL), extracted with ethyl acetate (2×50 mL), the combined organic layer was washed with brine (60 mL), dried over $Na_2SO_4$, filtered, and concentrated. The crude was purified by silica chromatography on a 100 g column using 0-60% ethyl acetate in hexanes as eluent to afford the white foam product 9a (3.2 g, 70%).

The compound 9a (3.2 g, 6.5 mmol, 1.0 eq) was dissolved in pyridine (20 mL) under stirring under nitrogen. Acetic anhydride (3.5 mL, 37 mmol, 5.7 eq) and DMAP (0.16 g, 1.3 mmol, 0.2 eq) were added and the reaction was heated at 75° C. for 19 hours. The reaction turned dark brown. It was diluted with heptane (2×125 mL) and concentrated under rotavap. The crude was purified by basic alumina chromatography on a 100 g column with 0-50% ethyl acetate in hexanes to afford the white foam product 9b (2.52 g, 82%).

The compound 9b (2.5 g, 5.8 mml, 1 eq) and 3-bromo-3,3-difluoro-1-TIPS-propyne (3.9 mL, 12.8 mmol, 2.2 eq) were dissolved in THF (75 mL) in an oven dried 3-necked 250 mL V-shaped flask fitted with thermometer, stirred bar and nitrogen. It was cooled to −78° C. n-BuLi (1.9 M in hexane, 6.7 mL, 12.8 mmol, 2.2 eq) was added dropwise over 30 minutes to maintain the reaction temperature under −74° C. The dark brown reaction solution was further stirred for 3 hours at −77° C. TLC showed most of the starting material consumed. The reaction was quenched with sat. aq. $NH_4Cl$ (25 mL), and 10% aq. NaSO4 (50 mL), extracted with DCM (2×50 mL), the combined organic layer was washed with brine (50 mL), dried over $Na_2SO_4$, filtered, concentrated and the crude was purified by basic alumina chromatography using 0-30% ethyl acetate in hexanes to afford the product 9c as beige foam (2.1 g, 55%).

The compound 9c (2.1 g, 1 eq) was dissolved in THF (21 mL) at rt under stirring, and aq. HCl (4M, 4 mL, 5 eq) was added. The resulting brown solution was stirred for 19 hours at rt. It was diluted with water (30 mL), extracted with DCM (2×40 mL), the combined organic was washed with brine (50 mL), dried over $Na_2SO_4$, filtered, concentrated and the crude was purified by silica gel chromatography using 0-50% ethyl acetate in hexanes to afford the beige foam product 9d (1.48 g, 76%).

The compound 9d (1.47 g, 1 eq) was dissolved in THF (15 mL) under stirring under nitrogen and this solution was cooled in ice bath. TBAF·3H2O (0.87 g, 1 eq) was added, the reaction solution turned nice purple, it was stirred at this temperature for 5 minutes, and the TLC showed complete conversion. The reaction was quenched with sat. aq. $NH_4Cl$ (30 mL), the crude product was extracted with DCM (2×35 mL), the combined organic was washed with brine (40 mL), dried over $Na_2SO_4$, filtered, concentrated and the crude was purified by silica gel chromatography using 0-60% ethyl acetate in hexanes to afford the beige foam product 9 (1.06 g, 84%). FT IR (ATR, $cm^{-1}$): 3370, 3231, 2957, 2229, 2129, 1729, 1646, 1599. $^1H$ NMR ($CDCl_3$, 300 MHz) δ 0.57 (s, 3H, H-18), 2.50 (s, 3H, $CH_3$), 2.92 (t, J=4.5 Hz, 1H, acetylenic-H), 4.39 (bs, 1H, H-11), 5.80 (s, 1H, H-4), 7.24 (m, 2H), 7.37 (s, 1H).

10

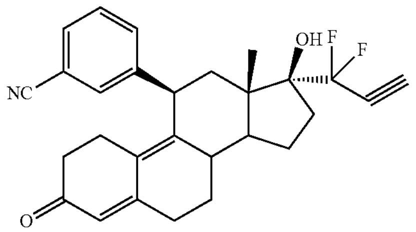

The product 10 was also prepared according to the procedure described in general procedure 2. 5-Bromobenzonitrile (5.0 g, 27.5 mmol, 2.5 eq) was dissolved in THF (50 mL) in an oven dried flask fitted with stirrer, thermocouple, and nitrogen. The solution was cooled to −10° C., and isopropyl-magnesium chloride lithium chloride in THF (1.3 M, 21.1 mL, 27.5 mmol, 2.5 eq) was added dropwise keeping the internal temperature below −3° C. during the addition. The pale reaction solution was stirred at −2 to 0° C. for 3 hours. CuCl (30 mg) was added at 0° C., followed by the addition of the epoxide b (solid, 3.63 g, 11.0 mmol, 1.0 eq). The temperature of reaction went as high as 10° C. and then started falling to 5° C. The reaction turned dark brown, and it was stirred for 45 minutes at this temperature. The TLC showed complete consumption of the epoxide. The reaction was quenched with sat. aq. $NH_4Cl$ (25 mL), diluted with 10% aq. $Na_2SO_4$ (50 mL), extracted with DCM (2×50 mL), the combined organic layer was washed with brine (60 mL), dried over $Na_2SO_4$, filtered, and concentrated. The crude was purified by silica chromatography on a 100 g column using 0-60% ethyl acetate in hexanes as eluent to afford the white foam product 10a (4.1 g, 86%).

The compound 10a (4.1 g, 9.5 mmol, 1.0 eq) was dissolved in pyridine (20 mL) under stirring under nitrogen. Acetic anhydride (4.5 mL, 47.3 mmol, 5.0 eq) and DMAP (0.23 g, 1.9 mmol, 0.2 eq) were added and the reaction was heated at 75° C. for 19 hours. The reaction turned dark brown. It was diluted with heptane (2×125 mL) and concentrated under rotavap. The crude was purified by basic alumina chromatography on a 100 g column with 2-50% ethyl acetate in hexanes to afford the white foam product 10b (2.84 g, 72%).

The compound 10b (2.83 g, 6.8 mml, 1 eq) and 3-bromo-3,3-difluoro-1-TIPS-propyne (4.6 mL, 15 mmol, 2.2 eq) were dissolved in THF (90 mL) in an oven dried 3-necked 250 mL V-shaped flask fitted with thermometer, stirred bar and nitrogen. It was cooled to −78° C. n-BuLi (1.9 M in hexane, 7.9 mL, 15 mmol, 2.2 eq) was added dropwise over 30 minutes to maintain the reaction temperature under −74° C. The dark brown reaction solution was further stirred for 3 hours at −76° C. TLC showed most of the starting material consumed. The reaction was quenched with sat. aq. $NH_4Cl$ (25 mL), and 10% aq. $Na_2SO_4$ (30 mL), extracted with DCM (2×50 mL), the combined organic layer was washed with brine (50 mL), dried over $Na_2SO_4$, filtered, concentrated and the crude was purified by basic alumina chromatography using 2-40% ethyl acetate in hexanes to afford the product 10c as beige foam (3.48 g, 79%).

The compound 10c (3.48 g, 1 eq) was dissolved in THF (25 mL) at rt under stirring, and aq. HCl (4M, 6.7 mL, 5 eq) was added. The resulting brown solution was stirred for 19 hours at rt. It was diluted with water (40 mL), extracted with DCM (2×50 mL), the combined organic was washed with brine (50 mL), dried over $Na_2SO_4$, filtered, concentrated and the crude was purified by silica gel chromatography using 0-40% ethyl acetate in hexanes to afford the beige solid product 10d (2.16 g, 66%).

The compound 10d (2.16 g, 1 eq) was dissolved in THF (20 mL) under stirring under nitrogen and this solution was cooled in ice bath. TBAF·3H2O (1.13 g, 1 eq) was added, the reaction solution turned purple, it was stirred at this temperature for 5 minutes, and the TLC showed complete conversion. The reaction was quenched with sat. aq. $NH_4Cl$ (30 mL), the crude product was extracted with DCM (2×45 mL), the combined organic was washed with brine (60 mL), dried over $Na_2SO_4$, filtered, concentrated and the crude was purified by silica gel chromatography using 0-60% ethyl acetate in hexanes to afford the beige solid product 10 (1.30 g, 84%). $^1H$ NMR ($CDCl_3$, 300 MHz) δ 0.54 (s, 3H, H-18), 2.91 (t, J=6 Hz, 1H, acetylenic-H), 4.43 (bs, 1H, H-11), 5.79 (s, 1H, H-4), 7.43 (m, 4H).

11

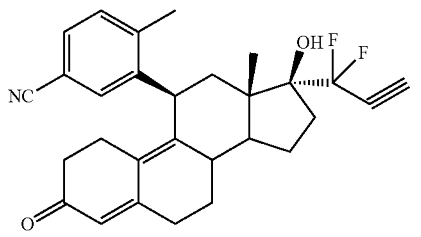

The product 11 was also prepared according to the procedure described in general procedure 2. 3-Bromo-4-methylbenzonitrile (5.0 g, 25.5 mmol, 2.2 eq) was dissolved in THF (50 mL) in an oven dried flask fitted with stirrer, thermocouple, and nitrogen. The solution was cooled to −10° C., and isopropyl-magnesium chloride lithium chloride in THF (1.3 M, 19.6 mL, 25.5 mmol, 2.2 eq) was added dropwise keeping the internal temperature below −3° C. during the addition. The pale reaction solution was stirred at −2 to 0° C. for 5 hours (the reaction temperature went to 4° C. at one point which was corrected to 0° C.). CuCl (66 mg) was added at 0° C., followed by the addition of the epoxide b (solid, 3.8 g, 11.5 mmol, 1.0 eq). The temperature of reaction went as high as 6.6° C. and then started falling to 5° C. The reaction turned dark brown, and it was stirred for 60 minutes at this temperature. The TLC showed incomplete consumption of the epoxide. The reaction was quenched with sat. aq. $NH_4Cl$ (25 mL), diluted with 10% aq. $Na_2SO_4$ (50 mL), extracted with DCM (2×50 mL), the combined organic layer was washed with brine (60 mL), dried over $Na_2SO_4$, filtered, and concentrated. The crude was purified by silica chromatography on a 100 g column using 0-60% ethyl acetate in hexanes as eluent to afford the white crystalline product 11a (1.45 g, 28%).

The compound 11a (1.45 g, 3.2 mmol, 1.0 eq) was dissolved in pyridine (15 mL) under stirring under nitrogen. Acetic anhydride (1.5 mL, 16.2 mmol, 5.0 eq) and DMAP (0.079 g, 0.64 mmol, 0.2 eq) were added and the reaction was heated at 73° C. for 19 hours. The reaction turned dark brown. It was diluted with heptane (2×100 mL) and concentrated under rotavap. The crude was purified by basic alumina chromatography on a 100 g column with 2-40% ethyl acetate in hexanes to afford the white solid product 11b (0.56 g, 40%).

The compound 11b (0.56 g, 1.3 mml, 1 eq) and 3-bromo-3,3-difluoro-1-TIPS-propyne (0.88 mL, 2.9 mmol, 2.2 eq) were dissolved in THF (30 mL) in an oven dried 3-necked 250 mL V-shaped flask fitted with thermometer, stirred bar and nitrogen. It was cooled to −78° C. n-BuLi (1.9 M in hexane, 1.5 mL, 2.9 mmol, 2.2 eq) was added dropwise over 10 minutes to maintain the reaction temperature under −74° C. The dark brown reaction solution was further stirred for 1 hours at −76° C. TLC showed most of the starting material consumed. The reaction was quenched with sat. aq. $NH_4Cl$ (25 mL), and 10% aq. $Na_2SO_4$ (20 mL), extracted with DCM (2×50 mL), the combined organic layer was washed with brine (50 mL), dried over $Na_2SO_4$, filtered, concentrated and the crude 11c was used without purification.

The compound 11c (Crude from compound 11b, 1.3 mml, 1 eq) was dissolved in THF (5 mL) at rt under stirring, and aq. HCl (4M, 5 mL) was added. The resulting brown solution was stirred for 3 hours at rt. It was diluted with water (20 mL), extracted with DCM (2×30 mL), the combined organic was washed with brine (30 mL), dried over $Na_2SO_4$, filtered, concentrated and the crude was purified by silica gel chromatography using 0-40% ethyl acetate in hexanes to afford the beige solid product 11d (0.47 g, 58%, 2 steps).

The compound 11d (0.47 g, 1 eq) was dissolved in THF (10 mL) under stirring under nitrogen and this solution was cooled in ice bath. TBAF·$3H_2O$ (0.24 g, 1 eq) was added, the reaction solution turned purple, it was stirred at this temperature for 5 minutes, and the TLC showed complete conversion. The reaction was quenched with sat. aq. $NH_4Cl$ (20 mL), the crude product was extracted with DCM (2×25 mL), the combined organic was washed with brine (30 mL), dried over $Na_2SO_4$, filtered, concentrated and the crude was purified by silica gel chromatography using 0-40% ethyl acetate in hexanes to afford the beige solid product 11 (185 mg, 53%). $^1H$ NMR ($CDCl_3$, 300 MHz) δ0.78 (s, 3H, H-18), 2.47 (s, 3H, $CH_3$), 2.90 (t, J=6 Hz, 1H, acetylenic-H), 4.45 (d, J=9 Hz, 1H, H-11), 5.78 (s, 1H, H-4), 7.28 (m, 2H), 7.40 (dd, J=3, 9 Hz, 1H).

12

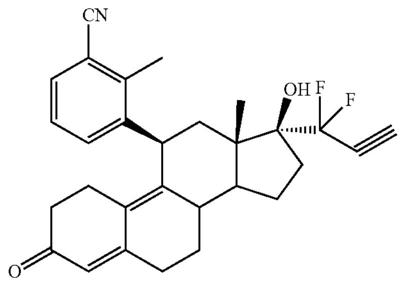

The product 12 was also prepared according to the procedure described in general procedure 2. 3-Bromo-2-methylbenzonitrile (5.0 g, 25.5 mmol, 2.2 eq) was dissolved in THF (60 mL) in an oven dried flask fitted with stirrer, thermocouple, and nitrogen. The solution was cooled to −7° C., and isopropyl-magnesium chloride lithium chloride in THF (1.3 M, 19.6 mL, 25.5 mmol, 2.2 eq) was added dropwise keeping the internal temperature below −3° C. during the addition. The pale reaction solution was stirred at −2 to 1° C. for 4 hours (the reaction temperature went to 4° C. at one point which was corrected to 0° C.). CuCl (50 mg) was added at 0° C., followed by the addition of the epoxide b (solid, 3.8 g, 11.5 mmol, 1.0 eq). The temperature of reaction went as high as 6.6° C. and then started falling to 5° C. The reaction turned dark brown, and it was stirred for 16 h at room temperature. The TLC showed incomplete consumption of the epoxide. The reaction was quenched with sat. aq. $NH_4Cl$ (25 mL), diluted with 10% aq. $Na_2SO_4$ (50 mL), extracted with DCM (2×50 mL), the combined organic layer was washed with brine (60 mL), dried over $Na_2SO_4$, filtered, and concentrated. The crude was purified by basic alumina chromatography on a 100 g column using 0-90% ethyl acetate in hexanes as eluent to afford the white foam product 12a (1.9 g).

The compound 12a (1.9 g, 3.2 mmol, 1.0 eq) was dissolved in pyridine (15 mL) under stirring under nitrogen. Acetic anhydride (1.5 mL, 16.2 mmol, 5.0 eq) and DMAP (0.079 g, 0.64 mmol, 0.2 eq) were added and the reaction was heated at 73° C. for 19 hours. The reaction turned dark brown. It was diluted with heptane (2×100 mL) and concentrated under rotavap. The crude was purified by basic alumina chromatography using 5-60% ethyl acetate in hexanes to afford the white foam 12b (0.80 g). NMR was good.

The compound 12b (0.80 g, 1.86 mml, 1 eq) and 3-bromo-3,3-difluoro-1-TIPS-propyne (1.26 mL, 4.1 mmol, 2.2 eq) were dissolved in THE (30 mL) in an oven dried 3-necked 250 mL RB flask fitted with thermometer, stirred bar and nitrogen. It was cooled to −78° C. n-BuLi (1.9 M in hexane, 2.2 mL, 4.1 mmol, 2.2 eq) was added dropwise over 15 minutes to maintain the reaction temperature under −74° C. The dark brown reaction solution was further stirred for 2 hours at −78° C. TLC showed most of the starting material consumed. The reaction was quenched with sat. aq. $NH_4Cl$ (25 mL), and 10% aq. $Na_2SO_4$ (20 mL), extracted with DCM (2×50 mL), the combined organic layer was washed with brine (50 mL), dried over $Na_2SO_4$, filtered, concentrated and the crude was purified by basic alumina chromatography on a 50 g column with 2-50% ethyl acetate in hexanes to afford the white solid product 12c (0.73 g).

The compound 12c (0.73, 1.3 mml, 1 eq) was dissolved in THE (10 mL) at rt under stirring, and aq. HCl (4M, 6 mL) was added. The resulting pale solution was stirred for 3 hours at rt. It was diluted with water (20 mL), extracted with DCM (2×30 mL), the combined organic was washed with brine (30 mL), dried over $Na_2SO_4$, filtered, concentrated and the crude was purified by silica gel chromatography on a 25 g column using 0-50% ethyl acetate in hexanes to afford the beige solid product 12d (0.33 g).

The compound 12d (0.33 g, 1 eq) was dissolved in THE (00 mL) under stirring under nitrogen and this solution was cooled under ice bath. TBAF·3H2O (0.17 g, 1 eq) was added, the reaction solution turned dark brown, it was stirred at this temperature for 5 minutes, and the TLC showed complete conversion. The reaction was quenched with sat. aq. $NH_4Cl$ (30 mL), the crude product was extracted with DCM (2×30 mL), the combined organic was dried over $Na_2SO_4$, filtered, concentrated and the crude was purified by silica gel chromatography using 0-60% ethyl acetate in hexanes to afford the beige product 12 (EC914) (0.20 g, 82%). $^1H$ NMR ($CDCl_3$, 300 MHz) δ 0.76 (s, 3H, H-18), 2.63 (s, 1H, $CH_3$-aryl), 2.90 (t, J=5.5 Hz, 1H, H-alkyne), 4.50 (d, J=8.7 Hz, 1H, H-11), 5.75 (s, 1H, H-4), 7.16 (t, J=8.5 Hz, 1H, H—Ar), 7.29 (d, J=8.6 Hz, 1H, H—Ar), 7.47 (d, J=8.7 Hz, 1H, H—Ar). Mass m/z found=462.2 [M+H].

13

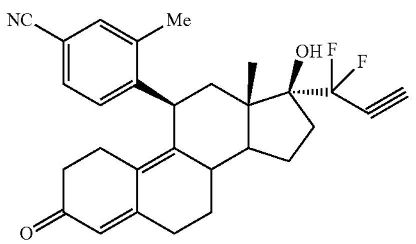

The product 13 was also prepared according to the procedure described in general procedure 2. 4-Bromo-3-methylbenzonitrile (5.0 g, 25.5 mmol, 2.2 eq) was dissolved in THF (50 mL) in an oven dried flask fitted with stirrer, thermocouple, and nitrogen. The solution was cooled to −1° C., and isopropyl-magnesium chloride lithium chloride in THE (1.3 M, 19.6 mL, 25.5 mmol, 2.2 eq) was added dropwise keeping the internal temperature below 1.7° C. during the addition over 30 minutes. The dark pale reaction solution was stirred at 2 to 5° C. for 90 minutes. CuCl (30 mg) was added at 0° C., followed by the addition of the epoxide b (solid, 3.8 g, 11.5 mmol, 1.0 eq). The temperature of reaction went as high as 8.6° C. and then started falling to 0° C. The reaction turned brown, and it was stirred for 18 h at room temperature. The TLC showed incomplete consumption of the epoxide with majority of the product. The reaction was quenched with sat. aq. $NH_4Cl$ (45 mL), stirred for 2 h in air, extracted with DCM (2×30 mL), the combined organic layer was dried over $Na_2SO_4$, filtered, and concentrated. The crude 3 was purified by basic alumina chromatography on a 100 g column using 0-90% ethyl acetate in hexanes as eluent to afford the white crystalline solid product 13a (2.68 g, 52%).

The compound 13a (2.62 g, 5.85 mmol, 1.0 eq) was dissolved in pyridine (9 mL) under stirring under nitrogen. Acetic anhydride (2.77 mL, 29.3 mmol, 5.0 eq) and DMAP (0.072 g, 0.58 mmol, 0.10 eq) were added and the reaction was heated at 69° C. for 17 hours. The reaction turned dark brown. It was diluted with heptane (2×50 mL) and concentrated under rotavap. The crude was purified by basic alumina chromatography using 0-30% ethyl acetate in hexanes to afford the white solid 13b (1.15 g, 46%).

The compound 13b (1.15 g, 2.68 mml, 1 eq) and 3-bromo-3,3-difluoro-1-TIPS-propyne (2.5 mL, 8.0 mmol, 3.0 eq) were dissolved in THF (35 mL) in an oven dried 3-necked 250 mL RB flask fitted with thermometer, stirred bar and nitrogen. It was cooled to −78° C. n-BuLi (2.5 M in hexane, 3.2 mL, 8.0 mmol, 3.0 eq) was added dropwise over 30 minutes to maintain the reaction temperature under below −75° C. The dark brown reaction solution was further stirred for 4 hours at −76° C. TLC showed most of the starting material consumed. The reaction was quenched with sat. aq. $NH_4Cl$ (50 mL), and 10% aq. $Na_2SO_4$ (20 mL), extracted with ethyl acetate (2×40 mL), the combined organic layer was washed with brine (50 mL), dried over $Na_2SO_4$, filtered, concentrated and the crude 13c was used without purification.

The compound 13c (crude, 2.68 mmol, 1 eq) was dissolved in THF (10 mL) at rt under stirring, and aq. HCl (4M, 10 mL, 40 mmol, 14.9 eq) was added. The resulting pale solution was stirred for 75 minutes at rt. It was diluted with water (15 mL), extracted with DCM (2×40 mL), the combined organic was washed with brine (30 mL), dried over $Na_2SO_4$, filtered, concentrated and the crude was purified by silica gel chromatography on a 50 g column using 0-20% ethyl acetate in hexanes to afford the beige solid product 13d (0.97 g, 58.7% over 2 steps).

The compound 13d (0.97 g, 1 eq) was dissolved in THF (20 mL) under stirring under nitrogen and this solution was cooled under ice bath. TBAF·3H2O (0.50 g, 1 eq) was added, the reaction solution turned dark brown, it was stirred at this temperature for 5 minutes, and the TLC showed complete conversion. The reaction was quenched with sat. aq. $NH_4Cl$ (30 mL), the crude product was extracted with ethyl acetate (2×30 mL), the combined organic was dried over $Na_2SO_4$, filtered, concentrated and the crude was purified by silica gel chromatography using 0-50% ethyl acetate in hexanes to afford the beige product 13 (EC915) (0.58 g, 85.6%). FT IR (ATR, $cm^{-1}$): 3309, 2953, 2224, 2135, 1649, 1590. $^1H$ NMR ($CDCl_3$, 300 MHz) δ 0.77 (s, 3H, H-18), 2.43 (s, 3H, $CH_3$), 2.89 (t, J=5.2 Hz, 1H, acetylenic-H), 4.47 (d, J=8.7 Hz, 1H, H-11), 5.74 (s, 1H, H-4), 7.16 (d, J=8.1 Hz, 1H), 7.36 (d, J=7.8 Hz, 1H), 7.45 (s, 1H).

Scheme A

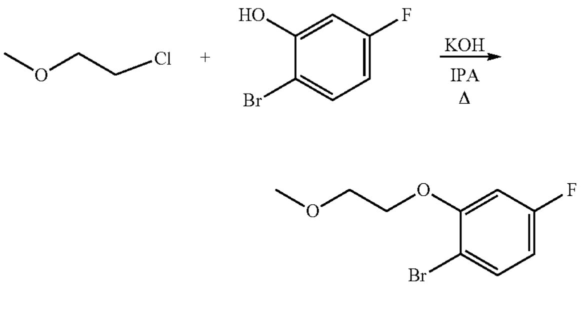

The methoxyethyl ether compound was started under reflux with the phenol (7.5 g), 2-chloroethylmethyl ether (3×3.1 g, 3 eq total) in isopropanol (50 mL) and KOH (2.6 g, 1.4 eq). The reaction was very slow, and it was left under reflux for 7 days (Ref: *J. Combinatorial Chemistry* 2003, 5, 606-609).

14

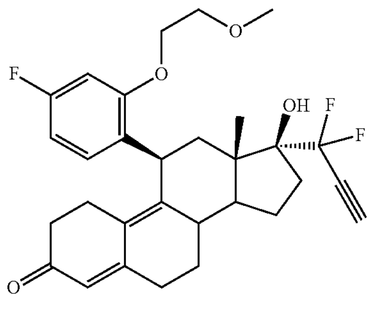

The product 14 was also prepared according to the procedure described in general method 1. FT IR (ATR, $cm^{-1}$): 3295, 2945, 2130, 1645, 1595. $^1H$ NMR ($CDCl_3$, 300 MHz) δ 0.74 (s, 3H, H-18), 2.87 (t, J=4.5 Hz, 1H, acetylenic-H), 3.44 (s, 3H, $CH_3$), 3.78 (m, 2H), 4.14 (m, 2H), 5.53 (d, J=9 Hz, 1H, H-11), 5.72 (s, 1H, H-4), 6.54 (m, 2H), 6.88 (dd, J=7.5, 7.5 Hz, 1H).

15

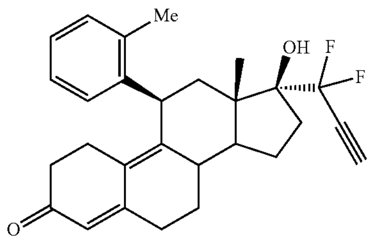

The compound 15 was synthesized according to the procedure described in general method 1. FT IR (ATR, $cm^{-1}$): 3371, 2929, 2119, 1642, 1596. $^1H$ NMR ($CDCl_3$, 300 MHz) δ 0.82 (s, 3H, H-18), 2.38 (s, 3H, $CH_3$), 2.88 (t, J=4.5 Hz, 1H, acetylenic-H), 4.44 (d, J=9 Hz, 1H, H-11), 5.71 (s, 1H, H-4), 7.02 (m, 3H), 7.13 (d, J=9 Hz, 1H).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An orally available LIF/LIFR inhibitor for the treatment of cancers that overexpress leukemia inhibitory factor (LIF), the compound having the structure (I), or the structure (D), or the structure (L):

(I)

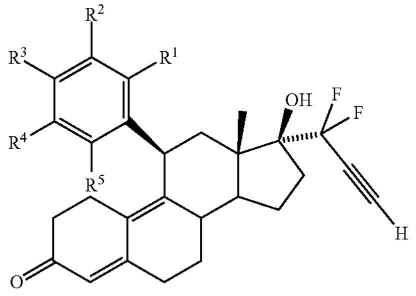

where, $R^2$ is $—O(CH_2)_n—COOR_6$, $—O(CH_2)_n—NR^6R^7$, or $—O(CH_2)_n—OR^6$;

each of $R^1$, $R^3$, $R^4$, or $R^5$ is hydrogen;

n=1 to 4; and $R^6$ and $R^7$ are, independently, H, alkyl, cycloalkyl, or $CD_3$;

(D)

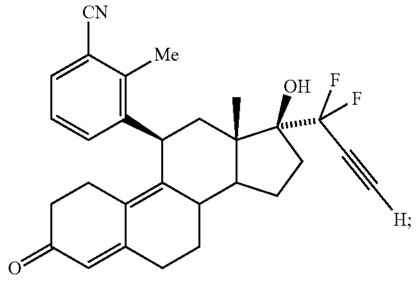

(L)

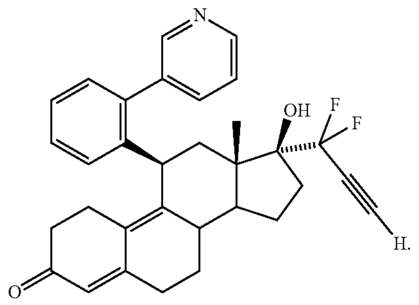

2. The LIF/LIFR inhibitor of claim 1, wherein the LIF/LIFR inhibitor has the structure (I-1), (J), or (K):

(I-1)

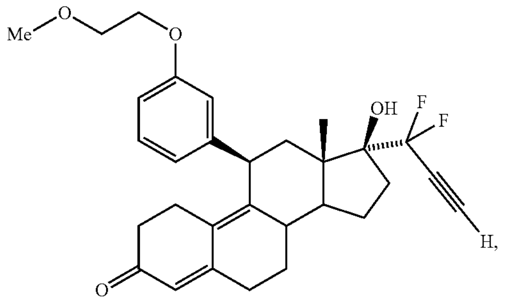

(J)

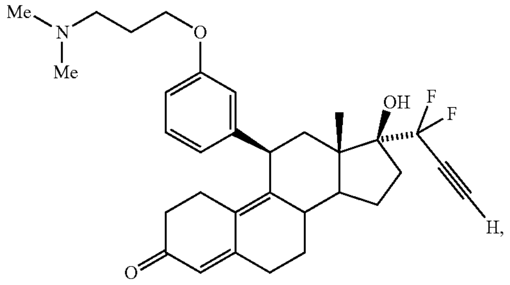

or (K)

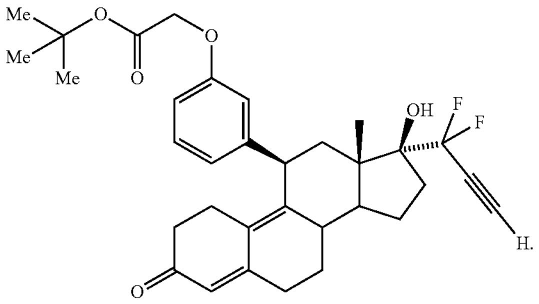

3. A pharmaceutical composition comprising a therapeutically effective amount of an LIF/LIFR inhibitor as described in claim 1 and a pharmaceutically acceptable carrier.

4. A method of treating cancers that overexpress leukemia inhibitory factor (LIF) in a subject comprising administering to a subject an effective amount of an LIF/LIFR inhibitor as described in claim 1.

5. A method of treating cancers that overexpress leukemia inhibitory factor (LIF) in a subject comprising administering to a subject an effective amount of an LIF/LIFR inhibitor as described in claim 1 and a taxane chemotherapeutic agent.

6. The method of claim 5, wherein the taxane chemotherapeutic agent is docetaxal.

7. The method of claim 5, wherein the cancer is a prostate cancer that overexpresses LIF.

* * * * *